(12) United States Patent
Lu et al.

(10) Patent No.: US 12,403,129 B2
(45) Date of Patent: Sep. 2, 2025

(54) ISOTOPE-ENRICHED 3-AMINO-1-PROPANESULFONIC ACID DERIVATIVES FOR THE TREATMENT OF CEREBROVASCULAR DISEASE

(71) Applicant: RISEN (SUZHOU) PHARMA TECH CO., LTD., Jiangsu (CN)

(72) Inventors: Jiasheng Lu, Shanghai (CN); Jiamin Gu, Suzhou (CN); Xianqi Kong, Dollard-des-Ormeaux (CA)

(73) Assignee: RISEN (SUZHOU) PHARMA TECH CO., LTD., Suzhou (CN)

( * ) Notice: Subject to any disclaimer, the term of this patent is extended or adjusted under 35 U.S.C. 154(b) by 207 days.

(21) Appl. No.: 17/523,160

(22) Filed: Nov. 10, 2021

(65) Prior Publication Data

US 2022/0202778 A1  Jun. 30, 2022

(51) Int. Cl.
| | |
|---|---|
| C07C 303/02 | (2006.01) |
| A61K 31/131 | (2006.01) |
| A61K 31/16 | (2006.01) |
| A61K 31/165 | (2006.01) |
| A61K 31/417 | (2006.01) |
| A61P 9/10 | (2006.01) |
| C07C 303/22 | (2006.01) |
| C07C 309/14 | (2006.01) |
| C07C 309/15 | (2006.01) |

(52) U.S. Cl.
CPC .......... *A61K 31/417* (2013.01); *A61K 31/131* (2013.01); *A61K 31/16* (2013.01); *A61K 31/165* (2013.01); *A61P 9/10* (2018.01)

(58) Field of Classification Search
CPC ... C07C 303/02; C07C 303/22; C07C 309/14; C07C 309/15
See application file for complete search history.

(56) References Cited

U.S. PATENT DOCUMENTS

| | | | |
|---|---|---|---|
| 5,840,294 A | 11/1998 | Kisilevsky et al. | |
| 5,972,328 A | 10/1999 | Kisilevsky et al. | |
| 6,310,073 B1 | 10/2001 | Kisilevsky et al. | |
| 6,603,008 B1 | 8/2003 | Ando et al. | |
| 6,670,399 B2 | 12/2003 | Green et al. | |
| 7,253,306 B2 | 8/2007 | Kong et al. | |
| 7,414,076 B2 | 8/2008 | Kong et al. | |
| 7,517,990 B2 | 4/2009 | Ito et al. | |
| 7,851,641 B2 | 12/2010 | Findeis | |
| 8,044,100 B2 | 10/2011 | Kong et al. | |
| 8,304,435 B2 | 11/2012 | Czarnik | |
| 8,557,994 B2 | 10/2013 | Dhanoa | |
| 8,642,801 B2 | 2/2014 | Kong et al. | |
| 8,669,275 B2 | 3/2014 | Czarnik | |
| 8,748,656 B2 | 6/2014 | Kong et al. | |
| 8,835,500 B2 | 9/2014 | Laurin et al. | |
| 8,835,654 B2 | 9/2014 | Kong et al. | |
| 8,927,553 B2 | 1/2015 | Dhanoa | |
| 9,249,149 B2 | 2/2016 | Silverman et al. | |
| 9,453,027 B2 | 9/2016 | Dhanoa | |
| 9,464,066 B2 | 10/2016 | Gopal | |
| 9,499,480 B2 | 11/2016 | Kong et al. | |
| 9,980,937 B2 | 5/2018 | Iwata et al. | |
| 10,106,524 B2 | 10/2018 | Trabanco-Suarez et al. | |
| 10,159,816 B2 | 12/2018 | Tsai et al. | |
| 10,188,636 B2 | 1/2019 | Roberts et al. | |
| 10,239,923 B2 | 3/2019 | Willbold et al. | |
| 10,246,468 B2 | 4/2019 | Bartels et al. | |
| 10,342,807 B2 | 7/2019 | Seong et al. | |
| 10,391,079 B2 | 8/2019 | Jackson | |
| 10,413,546 B2 | 9/2019 | Nishino et al. | |
| 10,471,029 B2 | 11/2019 | Tolar et al. | |
| 10,472,323 B2 * | 11/2019 | Lu .......................... | C07C 309/59 |
| 10,603,311 B2 | 3/2020 | Geva et al. | |
| 10,654,917 B2 | 5/2020 | Corte-Real et al. | |
| 10,954,188 B2 | 3/2021 | Lu et al. | |
| 11,020,360 B2 | 6/2021 | Kong et al. | |
| 11,191,742 B2 | 12/2021 | Abushakra et al. | |
| 2006/0079578 A1 | 4/2006 | Laurin et al. | |
| 2009/0076167 A1 | 3/2009 | Czarnik | |
| 2010/0120744 A1 | 5/2010 | Gant | |
| 2012/0214745 A1 | 8/2012 | Naicker et al. | |
| 2016/0331721 A1 | 11/2016 | Pan et al. | |
| 2018/0273471 A1 * | 9/2018 | Lu .......................... | A61P 25/28 |

(Continued)

FOREIGN PATENT DOCUMENTS

| | | |
|---|---|---|
| CN | 100528840 | 8/2009 |
| CN | 101600730 | 12/2009 |

(Continued)

OTHER PUBLICATIONS

"Accompany." Merriam-Webster.com Dictionary, Merriam-Webster, https://www.merriam-webster.com/dictionary/accompany. Accessed Nov. 1, 2023. (Year: 2023).*
Marchant, N., et al., "Cerebrovascular disease, beta-amyloid, and cognition in aging", Neurobiology of Aging (2012), 33: 1006.e25-1006.e36. (Year: 2011).*
Lednicer, D (2008). The Organic Chemistry of Drug Synthesis (7th ed.). Hoboken: John Wiley & Sons. p. 15. ISBN 978-0-470-18066-2. (Year: 2008).*
Elsevier. "Age-related GABA decline is associated with poor cognition". Medical press (Jan. 17, 2017), pp. 1-3, retrieved Aug. 29, 2024 from https://medicalxpress.com/news/2017-01-age-related-gabadecline-poor-cognition.html. (Year: 2017).*
Russak, E.M. et al., Impact of Deuterium Substitution on the Pharmacokinetics of Pharmaceuticals, Annals of Pharmacotherapy, Feb. 2019, 53(2), 211-216.

(Continued)

*Primary Examiner* — Joseph K McKane
*Assistant Examiner* — Sagar Patel
(74) *Attorney, Agent, or Firm* — BCF LLP

(57) ABSTRACT

There are provided methods for treating or preventing a cerebrovascular disease in a subject in need thereof comprising administering to the subject a therapeutically effective amount of an isotope-enriched compound or a pharmaceutical composition thereof, where the isotope-enriched compound has the general Formula (I) or is a pharmaceutically acceptable salt or ester thereof:

$$R^1R^2X-CR_2-CH_2-CH_2-SO_3H \quad (I).$$

2 Claims, 7 Drawing Sheets

(56) References Cited

U.S. PATENT DOCUMENTS

| | | | |
|---|---|---|---|
| 2019/0365771 | A1 | 12/2019 | Lichenstein et al. |
| 2020/0338040 | A1 | 10/2020 | Elmaleh |
| 2023/0295079 | A1* | 9/2023 | Lu .................... A61P 25/28 424/456 |
| 2024/0158343 | A1* | 5/2024 | Lu .................... C07B 59/001 |

FOREIGN PATENT DOCUMENTS

| | | | |
|---|---|---|---|
| CN | 102793694 | A | 11/2012 |
| CN | 104781240 | | 7/2015 |
| CN | 108623501 | A | 10/2018 |
| CN | 112791078 | A | 5/2021 |
| JP | 2010514674 | A | 5/2010 |
| WO | 1994022437 | | 10/1994 |
| WO | 1996028187 | | 9/1996 |
| WO | 2009019534 | | 12/2009 |
| WO | 2015143447 | | 9/2015 |
| WO | 2016182812 | | 11/2016 |
| WO | 201727582 | | 3/2017 |
| WO | 2017044840 | | 3/2017 |
| WO | 2017055540 | | 4/2017 |
| WO | 2018170590 | A1 | 9/2018 |

OTHER PUBLICATIONS

Kaur, S. et al., Deuteration as a tool for optimization of metabolic stability and toxicity of drugs, Global Journal of Pharmacy & Pharmaceutical Sciences, Mar. 2017, 1(4), 555566.
International Search Report and Written Opinion issued in co-pending International application No. PCT/CA2021/051600 on Jan. 18, 2022.
Briggs et al., Clinical Medicine, 16(3):247-253 (2016), Exhibit 2005 for Inter Partes Review No. IPR2021-00347, Apr. 15, 2021.
Cummings et al., Alzheimer's & Dementia, 2(4):222-232 (2016), Exhibit 2006 for Inter Partes Review No. IPR2021-00347, Apr. 15, 2021.
Godyn et al., Pharmacological Reports, 68(1):127-38 (2015), Exhibit 2007 for Inter Partes Review No. IPR2021-00347, Apr. 15, 2021.
Tofthagen, J. of the Advanced Practitioners in Oncology, 3(3):181-183 (2012), Exhibit 2025 for Inter Partes Review No. IPR2021-00347, Apr. 15, 2021.
Rothwell, Lancet, 356(9454):176-86 (2005), Exhibit 2028 for Inter Partes Review No. IPR2021-00347, Apr. 15, 2021.
Fisher et al., Curr Opin Drug Discov Devel, 9(1):101-9 (2006), Exhibit 2050 for Inter Partes Review No. IPR2021-00347, Oct. 6, 2021.
Paper No. 36 for the Inter Partes Review, Petitioner's second updated exhibit list, Mar. 3, 2022.
O'Brien, J.T. et al., Non-Alzheimer's dementia 3, Vascular dementia, The Lancet, vol. 386, pp. 1698-1706, Oct. 24, 2015.
Petition for Inter Partes Review of U.S. Pat. No. 10,472,323, Inter Pates Review No. IPR2021-00347, Dec. 18, 2020.
Exhibit 1002 for Inter Partes Review, Declartation of F. Peter Guengerich, Ph. D(2020).
Exhibit 1010 for Inter Partes Review, P. Atkins et al., Chemical Principles, Third Edition (2005).
Exhibit 1012 for Inter Partes Review, Morgan et al., "Old drugs yield new discoveries: Examples from the Prodrug, Chiral Switch, and site-selective deuteration strategies" in Barratt and Frail, Drug Repositiong: Bringing New Life to Shelved Assets and Existing Drugs (2012).
Exhibit 1013 for Inter Partes Review, L.E. Dyck et al., "Effects of deuterium substitution on the catabolismof β-Phenylethylamine: An in vivo study", J. Neurochemistry, 46:2, 399-404, 399 (1986).
Exhibit 1018 for Inter Partes Review, T.R. Browne, ed., Stable Isotopes in Pharmaceutical Research (1997).
Exhibit 1019 for Inter Partes REview, V.E. Anderson, "Isotope effects on enzyme-catalyzed reactions", Current Opinion in Structural Biology, 2:757-764 (1992).
Exhibit 1020 for Inter Partes Review, C. Hennig et al., "Secondary kinetic isotope effect in nucleophilic substitution", J. Phys. Chem. A, 110:3071-79 (2006).
Exhibit 1022 for Inter Partes Review, J. Belleau et al., "Effect of deuterium substitution in sympathomimetic amines on adrenergic responses", Science 133:102-104 (1961).
Exhibit 1024 for Inter Partes Review, J. Qui et al., "A new class of conformationally rigid analogues of 4-amino-5-nalopentanoic acids, potent inactivators of y-aminobutyric acird aminotransferase", J. Med. Chem, 43706-720, 712 (2000).
Exhibit 1025for Inter Partes Review, J. Mayer et al., "Homotaurine Metabolized to 3-Sulfopropanoate in Cupriavidus necator H16." J. Bacteriology, 191:6052-6058 (2009).
Exhibit 1021 for Inter Partes Review, O'Leary, "Multiple Isotope Effects on Enzyme-Catalyzed Reactions," Annu. Rev. Biochem., 58:377-401 (1989).
Exhibit 1023 for Inter Partes Review, Caldwell, J., et al., "An Introduction to Drug Disposition: the Basic Principles of Absorption, Distribution, Metabolism, and Excretion," Toxic Pathology, 23(2), 102-114, 110 (1995).
Exhibit 1026 for Inter Partes Review, T.S. Soper, et al., "Different Modes of Action of Inhibitors of Bacterial D-Amino Acid Transaminase." J. Biol. Chem., 256:4263-68 (1981).
Exhibit 1028 for Inter Partes Review, Yu et al., "Stereospecific Deuterium Substitution at the α-Carbon Position of Dopamine," Biochemical Pharmacology, 35:1027-36 (1986).
Exhibit 1031 for Inter Partes Review, Guengerich, F. P., "Kinetic deuterium isotope effects in cytochrome P450 reactions," Methods in Enzymology, vol. 596, Chap. 9, pp. 217-238 (2017).
Exhibit 1034 for Inter Partes Review, R. I. Feldman and H Weiner, "Horse Liver Aldehyde Dehydrogenase," J. Biol. Chem. 247 (1), 267-272 (1972).
Exhibit 1027 for Inter Partes Review, G. Burnett et al., "Mechanism-based Inaction of Pig Heart LAlanine Transaminase by L-Propargylglcine," J. Biol. Chem., 255:3487-3497 (1980).
Exhibit 1029 for Inter Partes Review, P.H. Yu, "Deuterium Isotope Effect in γ-Aminobutyric Acid Transamination," J. Neurochemistry, 48:440-446, 443 (1987).
Exhibit 1030 for Inter Partes Review, M.A. Rishavy, et al., "13C and 15N Kinetic Isotope Effects on the Reaction of Aspartate Aminotransferase," Biochemistry, 27:7546-51 (2000).
Exhibit 1032 for Inter Partes Review, C. Walsh, Enzymatic Reaction Mechanisms, Freeman, New York, pp. 796-797, (1979).
Exhibit 1033 for Inter Partes Review, Miller et al., "Structure-Activity Relationships in the Oxidation of Para-Substituted Benzylamine Analogues by Recombinant Human Liver Monoamine Oxidase." Biochemistry 38:41, 13670-13683 (1999).
Exhibit 1035 for Inter Partes Review, B. Yoval-Sánchez et al., "New insights into the half-of-the-sites reactivity of human aldehyde dehydrogenase 1A1," Proteins 81 (8), 1330-1339 (2013).
Exhibit 1036 for Inter Partes Review, Guengerich, F. P., "Cytochrome P450 and Chemical Toxicology," Chem. Res. Toxicol. 2008, 21, 1, 70-83.
Exhibit 1037 for Inter Partes Review, Alzheon Press Release, "Alzheon Presents Positive Results of ALZ-801 Clinical Studies that Lead to Advancement to Pivotal Phase 3 Study in Alzheimer's Patients with APOE4/4" (Jul. 25, 2016).
Exhibit 1014 for Inter Partes Review, Anslyn, et al. Modern Physical Organic Chemistry (2006).
Exhibit 1011 for Inter Partes Review, CRC Handbook of Chemistry and Physics, 95th Edition (2015).
Shoo, L. et al., The kinetic isotope effect in the search for deuterated drugs, Drug News & Perpectives 2010, 23(6), 398-404.
Foster, A.B., Deuterieum isotope effects in the metabolism of drugs and xenobiotics: Implications for drug design, Advances in Drug Research, vol. 14, 1985.
Cecil Textbook of Medecine, 20th edition (1196), vol. 2, pp. 2050-2057.
Cecil Textbook of Medecine, 20th edition (1996), vol. 2, pp. 1992-1996.
FDA mulls drugs to slow late-stage Alzheimer's [online], retrieved on Sep. 23, 2003 from the Internet, URL: http://www.cnn.com/2003/HEALTH/conditions/09/24/Alzheimers.drug.ap/index.html.

(56) References Cited

OTHER PUBLICATIONS

Courtyn, J. et al., Synthesis of 11C-labelled acamprosate for PET studies, J. Labelled Cpd. Radiopharm, 2001, vol. 44, pp. 643-651.
Zornoza, T. et al., Evidence of a flip-flop phenomenon in acamprosate pharmacokinetics: an in vivo study in rats, Biopharm, Drug Dispos., 2006, vol. 27, pp. 305-311.
Zornoza, T. et al., Disposition of acamprosate in the rat: Influence of probenecid, Biopharm. Drug Dispos., 2002, vol. 23, pp. 283-291.
Saivin, S. et al., Clinical Pharmacokinetics of Acamprosate, Clin. Pharmacokinet., 1998, vol. 35, pp. 331-345.
Chabenat, C. et al., Physicochemical, pharmacological and pharmacokinetic study of a new GABAergic compound, calcium acetylhomotaurinate, Methods and Findings in Experimental and Clinical Pharmacology, 1998, vol. 10, pp. 311-317 (abstract only).
Buteau, Kristen C., "Deuterated Drugs: Unexpectedly nonobvious?", 10 J. High Tech. L. 22, 2009, 22-74.
Timmins, Graham S., "Deuterated Drugs : where are we now?", Expert Opin Ther Pat. Oct. 2014; 24(10): 1067-1075.
Decision Granting Institution of Inter Partes Review, Inter Partes Review No. IPR2021-00347, Jul. 14, 2021.
Patent Owner Response, Inter Partes Review No. IPR2021-00347, Oct. 6, 2021.
Declaration of Jonathan L. Sessler, Ph.D., Exhibit 2042 for Inter Partes Review No. IPR2021-00347, Oct. 6, 2021.
Declaration of Steven L. Wagner, Ph.D., Exhibit 2068 for Inter Partes Review No. IPR2021-00347, Oct. 6, 2021.
Rowley et al., J Med Chem, 40(25):4053-68 (1997), Exhibit 2096 for Inter Partes Review No. IPR2021-00347, Oct. 6, 2021.
Deutetrabenazine (Austedo) Clinical Pharmacology and Biopharmaceutical Review (Apr. 2016)—Part 1 of 3, Exhibit 2095 for Inter Partes Review No. IPR2021-00347, Oct. 6, 2021.
Deutetrabenazine (Austedo) Clinical Pharmacology and Biopharmaceutical Review (Apr. 2016)—Part 2 of 3, Exhibit 2095 for Inter Partes Review No. IPR2021-00347, Oct. 6, 2021.
Deutetrabenazine (Austedo) Clinical Pharmacology and Biopharmaceutical Review (Apr. 2016)—Part 3 of 3, Exhibit 2095 for Inter Partes Review No. IPR2021-00347, Oct. 6, 2021.
CAS Registry Entry for Tramiprosate, Exhibit 2030 for Inter Partes Review No. IPR2021-00347, Oct. 6, 2021.
CAS Registry Entry for D2-tramiprosate, Exhibit 2031 for Inter Partes Review No. IPR2021-00347, Oct. 6, 2021.
CAS Registry Entry for Val-APS, Exhibit 2032 for Inter Partes Review No. IPR2021-00347, Oct. 6, 2021.
Exhibit 2026 for Inter Partes Review, IDS considered on Jan. 2, 2019 and Jul. 9, 2018 in U.S. Appl. No. 15/476,255 now U.S. Pat. No. 10,472,323.
Exhibit 2041 for Inter Partes Review, Videoconference deposition of Peter Guengerich, Ph. D., Sep. 28, 2021.
Exhibit 2066 for Inter Partes Review, U.S. Appl. No. 15/476,255, filed Mar. 31, 2017.
Exhibit 2098 for Inter Partes Review, Teva Pharmaceutical Inndustries Ltd., Report of foreign private issuer pursuant to Rule 13a-16 or 15d-16 under the Securities Exchange Act of 1934, May 2016.
Exhibit 3001 for Inter Partes Review, Aisen P. S. et al., Tramiprosate in mild-to-moderate Alzheimer's disease—a randomized, double-blind, placebo-controlled, multi-centre study (the Alphase Study), Arch Med Sci 2011, 7, 1: 102-111, 2011.
Exhibit 1043 for Inter Partes Review, Harbeson S.L et al., Deuterium Medicinal Chemistry: A New Approach to Drug Discovery and Development, Medchem News No. 2, May 2014.
Exhibit 1044 for Inter Partes Review, Ma Y. et al., Synthesis of Homotaurine and 1-substituted Homotaurines from a, b-Unsaturated Nitriles, Synthesis 2012, 44, 2225-2230, Jun. 13, 2012.
Exhibit 1045 for Inter Partes Review, CAS Reaction Search, Dec. 6, 2021.
Exhibit 1047 for Inter Partes Review, Errata to Transcript of Sep. 28, 2021 deposition of F. Peter Guengerich.
Exhibit 1048 for Inter Partes Review, Deposition of Jonathan L. Sessler, Ph.D., Dec. 8, 2021.
Exhibit 1050 for Inter Partes Review, Manzano S. et al., A Review on Tramiprosate (Homotaurine) in Alzheimer's Disease and Other Neurocognitive Disorders, Frontiers in Neurology, vol. 11, Article 614, Jul. 2020.
Exhibit 1051 for Inter Partes Review, Martorana A. et al., Homotaurine induces measurable changes of short latency afferent inhibition in a group of mild cognitive impairment individuals, Frontiers in Aging Neuroscience, vol. 6, Article 254, Sep. 2014.
Exhibit 1052 for Inter Partes Review, Spalletta G. et al., Homotaurine Effects on Hippocampal Volume Loss and Episodic Memoty in Amnestic Mild Cognitive Impairment, Journal of Alzheimer's Disease 50 (2016) 807-816.
Exhibit 1053 for Inter Partes Review, Bossu P. et al., Anti-inflammatory Effects of Homotaurine in Patients with Amnestic Mild Cognitive Impairment, Frontiers in Aging Neuroscience, vol. 10, Article 285, Nov. 2018.
Exhibit 1054 for Inter Partes Review, Abushakra S. et al., Clinical Effects of Tramiprosate in APOE4/4 Homozygous Patients with Mild Alzheimer's Disease Suggest Disease Modification Potential, The Journal of Prevention of Alzheimer's Disease, vol. 4, No. 3, 2017.
Exhibit 1055 for Inter Partes Review, Sabbagh M.N., Clinical Effects of Oral Tramiprosate in APOE4/4 Homozygous Patents with Mild Alzheimer's Disease Suggest Disease Modification, The Journal of Prevention of Alzheimer's Disease, vol. 4, No. 3, 2017.
Exhibit 1058 for Inter Partes Review, Azzi M. et al., Involvement of both Gaba-Dependant and -Independant Pathways in Tramiprosate Neuroprotective Effects Against Amyloid-Beta Toxicity, Neurodegenerative Dis 2007;4(suppl 1):1-350.
Exhibit 1059 for Inter Partes Review, Janssens de Varebeke P. et al., Formation of the neurotransmitter glycine from the anticonvulsant Milacemide is mediated by brain monoamine oxidase B, Journal of Neirochemistry, 1988.
Exhibit 1060 for the Inter Partes Review, Matsukawa M. et al., A screening system of prodrugd selective for MAO-A or MAO-B, NeuroToxicology 25, 293-302, 2004.
Exhibit 1061 for the Inter Partes Review, Fieser L.F. et al., Reagents for Organic Synthesis, 1967.
Exhibit 1062 for the Inter Partes Review, Wade L.G. Jr., Organic Chemistry, 5th edition, 2003.
Exhibit 1063 for the Inter Partes Review, March J., Advance Organic Chemistry, "Reactions, mechanisms, and structure", 3rd edition, 1985.
Exhibit 1064 for the Inter Partes Review, Mullard, A. Deuterated drugs draw heavier backing, Nature Reviews—Drug Discovery, vol. 15, Apr. 2016.
Exhibit 1065 for the Inter Partes Review, Teva Annonces Positive Top-Line Data from Second Phase III Study of SD-809 in Tardive Dyskinesia (TD), Sep. 22, 2016.
Exhibit 1066 for the Inter Partes Review, Guengerich, F.P et al., Methylene Oxidation of Alkyl Sulfates by Cytochrome P450BM-3 and a Role for Conformational Selection in Substrate Recognition, American Chemical Societe, ACS Publications, 2020.
Exhibit 1067 for the Inter Partes Review, De Strooper, B., Lessons from a Failed y-Secretase Alzheimer Trial, Cell 159, Nov. 6, 2014.
Exhibit 1068 for the Inter Partes Review, Sharma R. et al., Deuterium Isotope Effects on Drug Pharmacokinetics. I. System-Dependent Effects of Specific Deuteration with Aldehyde Oxidase Cleared Drugs, The American Society for Pharmacology and Experimental Therapeutics, Drug Metabolism and Disposition, vol. 40, No. 3, 2012.
Exhibit 1069 for the Inter Partes Review, Deposition of S. David Kimball, Ph.D., Feb. 24, 2022.
Exhibit 1071 for the Inter Partes Review, Kurtz K.A. et al., pH and Secondary Kinetic Isotope Effects on the Reaction of D-Amino Acid Oxidase with Nitroalkane Anions: Evidence for Direct Attack on the Flavin by Carbanions, J. Am. Chem. Soc, 1997, 119, 1155-1156.
Exhibit 1072 for the Inter Partes Review, Walsh, C. Enzymatic Reaction Mechanisms, 1977.
Exhibit 1073 for the Inter Partes Review, Cook P.F. et al., Enzyme Kinetics and Mechanism, 2007.
Paper No. 19 for the Inter Partes Review, Patent owner's contigent motion to amend pursuant to 37 CFR 42.121, Oct. 6, 2021.

(56) References Cited

OTHER PUBLICATIONS

Paper No. 34 for the Inter Partes Review, Petitioner's reply to Patent owner response, Mar. 3, 2022.
Paper No. 35 for the Inter Partes Review, Petitioner's opposition to contingent motion to amend, Mar. 3, 2022.
Shuangchan et al., Tramiprosate protects neurons against ischemic stroke by disrupting the interaction between PSD95 and nNOS, Neuropharmacology, vol. 83, p. 107-117, Apr. 24, 2014.

* cited by examiner

ISOTOPE-ENRICHED 3-AMINO-1-PROPANESULFONIC ACID DERIVATIVES FOR THE TREATMENT OF CEREBROVASCULAR DISEASE

CROSS-REFERENCE TO RELATED APPLICATIONS

This application claims the benefit of priority from Chinese application no. 202011258039.5 filed Nov. 11, 2020, the entire contents of which are hereby incorporated by reference.

FIELD

The present disclosure relates to the use of isotope-enriched 3-amino-1-propanesulfonic acid (3APS) and its derivatives, and compositions thereof, in the prevention and treatment of cerebrovascular disease, including vascular dementia and stroke.

BACKGROUND

Cerebrovascular disease (CVD) refers broadly to a variety of disorders of the cerebral vasculature, including cerebral atherosclerosis, thrombosis, stenosis, occlusion, cerebral arteritis, cerebral artery injury, cerebral aneurysms, intracranial vascular malformations, cerebral arteriovenous fistulas, and the like, which have in common the characteristic of causing ischemic or hemorrhagic accidents of the brain tissue. Cognitive impairment caused by ischemic or hemorrhagic cerebrovascular disease as well as global cerebral ischemia and hypoxia is called vascular dementia (VD), which is dominated by memory and cognitive deficits and is a dementia syndrome with impaired mental activity including memory, visuospatial, emotional, personality and other cognitive functions (e.g., calculation ability, abstract judgment ability). The prevalence of vascular dementia is not completely consistent among countries. In Europe and the United States, it is the second most common dementia after Alzheimer's disease, while the prevalence of VD in China accounts for about 60% of senile dementia. Vascular dementia leads to a decline in living ability, which can seriously affect the quality of life and cause a great burden to patients, families and society.

The clinical manifestations of VD mainly include early symptoms, localized neurological symptoms, and symptoms of dementia. The early stages of VD have no obvious manifestations, mostly somatic discomfort, and the more prominent manifestations with localized neurological symptoms include dysarthria, dysphagia, varying degrees of hemiplegia, aphasia, seizures, and urinary incontinence. As the condition worsens, in the presence of severe somatic comorbidities, intense mental impairment, especially acute cerebrovascular disease, the symptoms of dementia tend to increase in a stepwise manner, by the late-stage manifesting as generalized dementia, with impairment of memory, calculation, thinking, and/or self-knowledge. Personality can also change significantly. Current clinical practice for VD focuses on treating primary cerebrovascular diseases and preventing the occurrence of VD. For VD patients, vitamin E, vitamin C and *Ginkgo biloba* preparations are used for supportive treatments. There is currently no approved therapy for treating VD available.

Cerebral stroke, also known as "stroke" or "cerebrovascular accident (CVA)" or "apoplexy", is an acute cerebrovascular disease. Clinically, it is dominated by acute onset, mostly in middle-aged and elderly patients, who often present with hemiplegia, speech disorders, and the like. CVA refers to a group of disorders that cause brain tissue damage due to the sudden rupture of cerebral vessels or the failure of blood to flow into the brain due to blockage of blood vessels, including ischemic or hemorrhagic stroke. Ischemic stroke has a higher incidence than hemorrhagic stroke, accounting for about 75%-90% of the total number of strokes, while hemorrhagic stroke accounts for the remainder. Internal carotid artery and vertebral artery occlusion as well as stenosis can cause ischemic stroke. Most patients are elderly, generally above 40 years old. Stroke occurs more frequently in males than females, and severe cases can cause death. Stroke is characterized by high morbidity, mortality, and disability. When combining occurrence in both rural and urban areas, stroke is currently the leading cause of death and disability among Chinese adults.

The most common cause of stroke is a small embolus on the inner wall of a brain feeding vessel, which after sloughing leads to arterial embolism (ischemic stroke). It may also be due to cerebrovascular or thrombotic hemorrhage (hemorrhagic stroke). Heart valves in patients with coronary heart disease associated with atrial fibrillation (AF) are prone to mural thrombi, which can occlude cerebral vessels after emboli are dislodged and can also lead to ischemic stroke. Other factors include hypertension, diabetes mellitus, high blood lipids, and the like. Among them, hypertension is the most important risk factor for stroke incidence in the Chinese population, especially abnormally elevated blood pressure in the early morning. Early morning hypertension is the strongest independent predictor of stroke events. Indeed the risk of ischemic stroke was shown to be four times higher in the early morning hours than at other times, with a 44% increased risk for each 10 mmHg increase in early morning blood pressure (Kario, K. et al., J. Am. Soc. Hypertens, 2008, 2(6); 397-402).

The main cause of stenosis and occlusion of the internal carotid or vertebral arteries is atherosclerosis. Other causes include arterial intimal hyperplasia, hypertrophy due to collagenous diseases, hypertensive arterial changes, rheumatic heart disease or arteritis, hematological diseases, metabolic diseases, drug reactions, tumors, connective tissue diseases which induce carotid trauma, tumor compressing carotid arteries, carotid thrombosis associated with pediatric cervical lymphadenitis and tonsillitis, and congenital carotid tortuosity. These can all result in stenosis and occlusion of the internal carotid artery, or trigger stroke due to bleeding from a ruptured vessel. Vertebral artery ischemia can also be caused by cervical spondylosis with hyperostosis or entrapment of the skull base compressing the vertebral artery.

The most common symptoms of stroke are a sudden feeling of weakness on one side of the face, arm, or leg, sudden fainting, and unconsciousness. Other symptoms include sudden onset of numbness on one side of the face, arm, or leg; sudden onset of mouth deviation, hemiplegia, confusion, difficulty speaking or understanding; monocular or binocular visual difficulty; difficulty in walking; vertigo and/or loss of balance or coordination; severe headache without obvious cause; and fainting.

Severe stroke may cause permanent neurological damage, and in the acute phase, it may cause serious complications or even death if not promptly diagnosed or treated. Stroke can be divided into hemorrhagic and ischemic stroke, and different treatment modalities exist depending on the site of occurrence. Therapies that are specific for stroke include thrombolysis, antiplatelet therapy, early anticoagulation, and neuroprotection. Nonspecific therapies include antihypertensive therapy, management of glycemia, cerebral edema, and management of intracranial hypertension. Thrombolytic therapy can be an effective salvage treatment for stroke, but there are strict time requirements (e.g., the limit of intravenous thrombolysis is within 4.5 hours, and arterial thrombolysis can be limited similarly). For patients with apoplexy and hypertension, blood pressure should be controlled according to the guidelines for stroke in patients with pre-existing stroke with hypertension. The goal of blood pressure treatment is generally <140/90 mmHg in chronic or delayed stroke patients, and <130/80 mmHg in patients with hyperlipidemia and diabetes mellitus. The principles of antihypertensive treatment for stroke are smooth, long-lasting, and effective control of 24 h blood pressure (BP), especially in the early morning. All five commonly used antihypertensive drugs can exert their effects on stroke prevention or transient ischemia through antihypertensive effect, among which there is clear clinical evidence for efficacy of calcium antagonists (CCBS) in reducing the risk of stroke. Antihypertensive medication should usually be started at a low dose, with close observation of blood pressure levels and adverse effects, to keep blood pressure within the safe range (160/100 mmHg) whenever possible. Patients generally start at a low dose while on antihypertensive treatment, and it is prudent to start the treatment early in case of insufficient blood supply to the brain. Caution should be exercised in patients with elevated BP within 24 h of acute ischemic stroke onset. Patients with pre-existing conditions such as hypertension, diabetes, and hyperlipidemia may take a number of medications prophylactically, such as aspirin, β-blockers, angiotensin-converting enzyme inhibitors, statins, and the like.

The pathological phenomenon of apoplexy may be related to the neuronal nitric oxide synthase (nNOS) in the cytoplasm and the postsynaptic density on the cell membraneβ (PSD95). The activation of neuronal nitric oxide synthase (nNOS) mediated by N-methyl-D-aspartate receptor (NMDAR) is a key event in the occurrence of neuronal excitotoxicity. Many drugs have been developed around these two target molecules. However, as NMDAR and nNOS have very important physiological functions, their direct intervention often leads to serious side effects. It has been shown that blocking the combination of PSD95 and nNOS can protect nerve cells from damage (Li Zhou, et al., Nature medicine, (2010) 16 (12), 1349-1443). Zhou et al. showed that coupling of ischemia-induced nNOS and postsynaptic density protein PSD95 is a key molecular mechanism underlying cerebral ischemic injury and blocking this coupling can effectively protect against cerebral ischemic injury. Further, this kind of protective effect on nerve injury caused by cerebral ischemia can avoid the side effects (such as learning and memory impairment) caused by direct intervention of NMDAR or nNOS; does not lead to aggressive and other behavioral abnormalities in animals; and does not have many of the side effects of other drugs on receptors.

Although there are five main classes of stroke therapeutics (brain circulation promoting class; nootropic class; neurotrophic class; neuroprotective class; and neurostimulant class), there is no specific medicine for the treatment of stroke patients, and only symptomatic and supportive treatment drugs, such as neuroprotective agents and agents for improving cerebral vascular circulation, are generally used (for review, see Prabhakaran, Jama, S. et al., 2015, 313 (14): 1451-62; https://baike.baidu.com/medicine/disease/%E8%84%910%E5%8D%92%E4%B8%AD/2204237?from=lemma). There is an urgent need for novel agents that can effectively treat or prevent stroke and its complications.

Tramiprosate is an investigational product candidate for the treatment of Alzheimer's disease. Tramiprosate was the subject of Phase III clinical trials in North America and Europe (Wright, T. M., Drugs of Today (2006), 42(5): 291-298). Results from these clinical studies have been published (Journal of Nutrition, Health & Aging (2009), 13(6), 550-557; Journal of Nutrition, Health & Aging (2009), 13(9), 808-812; Archives of Medical Science (2011), 7(1), 102-111; Journal of Alzheimer's Disease (2016), 50(3), 807-816; Aging: Clinical and Experimental Research (2012), 24(6), 580-587).

It is known that tramiprosate is metabolized both in vitro and in vivo (U.S. Pat. No. 8,748,656). Tramiprosate is extensively metabolized in vivo to produce three potential metabolites: 2-carboxyethanesulfonic acid, 3-hydroxy-1-propanesulfonic acid, and 3-acetylamino-1-propansulfonic acid. The only major metabolite produced in mice, rats, dogs, and humans is 2-carboxyethanesulfonic acid. This metabolism of tramiprosate can have significant effect on its pharmacokinetic profile and accordingly its pharmaceutical efficacy. In order to increase therapeutic effectiveness of 3APS, attempts have been made to increase overall bioavailability, for example by increasing stability or reducing metabolism. One such approach is the use of prodrugs and derivatives of 3APS that will generate 3APS in vivo after administration to a subject (see, for example, U.S. Pat. No. 8,748,656 and PCT International Application Publication No. WO 2015/143447, the contents of which are hereby incorporated by reference in their entirety). Another such approach is the use of isotope-enriched 3APS and derivatives thereof (see, for example, U.S. Pat. No. 10,472,323, the contents of which are hereby incorporated by reference in their entirety).

Foreign substances including compounds and other therapeutic agents are often metabolized to facilitate their elimination from the body. For example, various enzymes such as cytochrome P450 enzymes, esterases, proteases, reductases, dehydrogenases, transaminases, and monoamine oxidases, can react with foreign substances and catalyze their conversion to more polar metabolites for renal excretion. The resultant metabolites can have substantially different pharmacokinetic, pharmacodynamic, and acute and long-term toxicity profiles relative to the parent compounds.

Such metabolic reactions frequently involve the oxidation of a carbon-hydrogen bond to a carbon-oxygen or a carbon-carbon π-bond. Carbon-hydrogen bond strength is directly proportional to the absolute value of the ground-state vibrational energy of the bond. This vibrational energy depends on the mass of the atoms that form the bond and increases as the mass of one or both of the atoms making the bond increases. Since deuterium (D) has twice the mass of protium (H), a carbon-deuterium (C-D) bond is stronger than the corresponding carbon-protium (C-$^1$H) bond. If a C-$^1$H bond is broken during a rate-determining step of a metabolic reaction, then substituting a deuterium for that protium will cause a decrease in the reaction rate.

Deuterium is a stable and non-radioactive isotope of hydrogen which has approximately twice the mass of protium, which is the most common isotope of hydrogen. Deuteration of pharmaceuticals to improve pharmacokinetics and pharmacodynamics has been demonstrated previously. For example, SD-809, a deuterated drug (deutetrabenazine), has been used for the treatment of Huntington's disease. Such isotope-enrichment can potentially affect a therapeutic agent's metabolism, release from prodrugs and derivatives, absorption, and/or clearance, significantly altering the agent's pharmacokinetic profile.

International application no. PCT/CA2018/050334 (WO2018/170590; corresponding to U.S. Pat. Nos. 10,472, 323 and 10,954,188) describes isotope-enriched 3-amino-1-propanesulfonic acid (3APS) and derivatives thereof, compositions thereof, and methods of use thereof for the prevention and/or treatment of amyloid-β related diseases, such as Alzheimer's disease, cerebral amyloid angiopathy, and hereditary cerebral hemorrhage.

However, since tramiprosate (3APS) is believed to act by reducing amyloid aggregation, deposition and/or load of amyloid in the brain through binding to soluble Aβ peptide, such references are concerned only with prevention and treatment of amyloid-β related diseases. Although it has been shown that tramiprosate (3APS) can protect neurons from ischemic stroke by blocking the interaction between PSD95 and nNOS (Wu, Chuangchan et al., Neuropharmacology (2014), 83, 107-117), there are no clinical reports on potential efficacy of tramiprosate in the prevention or treatment of cerebrovascular conditions or disorders such as stroke which are not amyloid-β related. CN102793694B (International PCT Application Publication No. WO2014026557) reported the application of tramiprosate (3APS) derivatives in treating stroke, but only 3-amino-1-propanesulfonic acid (3APS), 3APS ethyl ester, and 3-(acetylamino)-1-propanesulfonic acid calcium salt were tested, and no systematic study was conducted on the metabolism and efficacy of 3APS derivatives in the prevention or treatment of non-amyloid-β related cerebrovascular diseases such as stroke and vascular dementia.

SUMMARY

It is an object of the present invention to ameliorate at least some of the deficiencies present in the prior art. Embodiments of the present technology have been developed based on the inventors' appreciation that there is a need for methods for treating and/or preventing non-amyloid-β related cerebrovascular diseases, such as vascular dementia and stroke. These and other needs can be satisfied by the disclosure herein of methods of treating and/or preventing cerebrovascular diseases using isotope-enriched 3-amino-1-propanesulfonic acid (3APS) and derivatives and compositions thereof.

Specifically, the present disclosure provides methods of treating or preventing non-amyloid-β related cerebrovascular diseases such as stroke and vascular dementia, comprising administering to a subject in need thereof a therapeutically effective amount of an isotope-enriched compound, or a pharmaceutical composition thereof. Isotope-enriched compounds for use in the methods of the present disclosure include 3-amino-1-propanesulfonic acid (3APS) derivatives and/or prodrugs as described further hereinbelow. We demonstrate herein efficacy of such compounds in several animal models of non-amyloid-β related cerebrovascular disease. Without wishing to be limited by theory, such isotope-enriched 3APS derivatives and/or prodrugs can improve the efficacy of 3APS in the treatment and/or prevention of cerebrovascular diseases, for example by increasing drug bioavailability, increasing drug stability, and/or reducing drug metabolism.

In a first broad aspect, there are provided compounds of Formula (I), or pharmaceutically acceptable salts or esters thereof, for use in the treatment and/or prevention of cerebrovascular diseases:

$$R^1R^2X-CR_2-CH_2-CH_2-SO_3H \qquad (I)$$

where: $R^1$ and $R^2$ are independently a hydrogen of natural abundance or a protecting group that is of natural abundance or isotope-enriched, the protecting group being selected from acyl, carbonyl, thiocarbonyl, and carbamoyl groups; X is a nitrogen of natural abundance, an $^{15}$N-enriched nitrogen ($^{15}$N) or a combination thereof; and R is a hydrogen of natural abundance, a deuterium (D) or a combination thereof, provided that $R^1$, $R^2$, X and R are not all atoms of natural abundance. In some embodiments, R is deuterium (D). In some embodiments, X is $^{15}$N. In some embodiments, R is D and X is $^{15}$N. In some embodiments, when X and R are atoms of natural abundance (i.e. X is $^{14}$N and R is H), at least one atom in $R^1$ and/or $R^2$ is isotope enriched. In one embodiment of Formula (I), $R^1$ is an amino acid residue with or without isotope-enrichment and $R^2$ is a hydrogen of natural abundance.

In some embodiments of compounds of Formula (I), $R^1$ is an amino acid residue with or without one or more isotopically-enriched oxygen and/or nitrogen atom, and $R^2$ is a hydrogen atom of natural abundance.

In some embodiments of compounds of Formula (I), R is deuterium (D) and X is a nitrogen of natural abundance. In some embodiments of compounds of Formula (I), R is deuterium (D), and X, $R^1$, and $R^2$ are all atoms of natural abundance. In some embodiments of compounds of Formula (I), R is deuterium (D), and at least one of X, $R^1$, and $R^2$ has one or more atom or element in an isotope-enriched form.

In some embodiments of compounds of Formula (I), R is a hydrogen of natural abundance and X is $^{15}$N. In some embodiments of compounds of Formula (I), X is $^{15}$N, and R, $R^1$, and $R^2$ are all atoms of natural abundance. In some embodiments of compounds of Formula (I), X is $^{15}$N, and at least one of R, $R^1$, and $R^2$ has one or more atom or element in an isotope-enriched form.

In some embodiments of compounds of Formula (I), $R^1$ and $R^2$ are not acetyl.

In a second broad aspect, there are provided compounds of Formula II, or pharmaceutically acceptable salts or esters thereof, for use in the treatment and/or prevention of cerebrovascular diseases:

$$H_2X-CR_2-CH_2-CH_2-SO_3H \qquad (II)$$

where X is a nitrogen of natural abundance, an N-15 isotope-enriched nitrogen (also referred to herein as "$^{15}$N-enriched nitrogen" or "$^{15}$N") or a combination thereof, and R is a hydrogen of natural abundance, a deuterium (D) or a combination thereof, provided that X and R are not both atoms of natural abundance at the same time (in other words, R is not a hydrogen of natural abundance when X is a nitrogen of natural abundance, e.g., when X is a nitrogen of natural abundance, R is D). In some embodiments, R is a hydrogen of natural abundance and X is $^{15}$N. In some embodiments, R is D and X is a nitrogen of natural abundance. In some embodiments, R is D and X is $^{15}$N.

In a third broad aspect, there are provided compounds of Formula III, or pharmaceutically acceptable salts or esters thereof, for use in the treatment and/or prevention of cerebrovascular diseases:

$$R^3-Y-XH-CR_2-CH_2-CH_2-SO_3H \qquad (III)$$
$$\overset{\|}{Z}$$

where X and R are as defined above; Y is a carbon of natural abundance, a $^{13}$C-enriched carbon ($^{13}$C) or a combination thereof, Z is a sulfur, an oxygen of natural abundance, an $^{18}$O-enriched oxygen ($^{18}$O), an $^{17}$O-enriched oxygen ($^{17}$O) or a combination thereof; and $R^3$ is a substituting group selected from substituted or unsubstituted alkyl, aryl, amino alkyl, amino arylalkyl, heterocyclyl, alkoxyl, alkylthio, alkylamino, acyloxyl, and thioacyloxyl; provided that at least one of X, R, Y and Z is not an atom of natural abundance. In some embodiments, R is not a hydrogen of natural abundance when X is a nitrogen of natural abundance.

In one embodiment of Formula (III), $R^3$, Y, and Z taken together form an acyl group connected to X, forming an amide bond linkage, and the acyl group is not an acetyl group. In another embodiment, $R^3$ is the side chain of an amino acid residue and $R^3$, Y, and Z taken together form an acyl group connected to X. The amino acid may be an L-amino acid, a D-amino acid, or a mixture of L and D forms. The amino acid may be a natural or an unnatural amino acid. In a particular embodiment, the amino acid is an L-amino acid. In one embodiment, the amino acid is a natural (i.e., naturally-occurring) L-amino acid.

In some embodiments, there are provided compounds of Formula IV and Formula V, or pharmaceutically acceptable salts or esters thereof, for the treatment and/or prevention of cerebrovascular diseases:

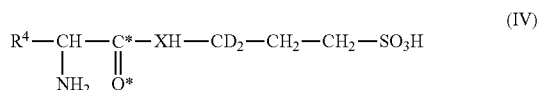

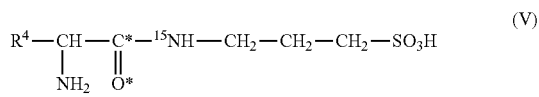

where $R^4$ is a side chain of a natural or unnatural amino acid; O* is an oxygen atom of natural abundance or an isotope-enriched oxygen atom ($^{18}$O, $^{17}$O, or a combination thereof); and C* is a carbon atom of natural abundance or an isotope-enriched carbon atom (e.g., $^{13}$C). In one embodiment, at least one of O* and C* is an isotope-enriched atom. The natural or unnatural amino acid may be an L-amino acid, a D-amino acid, or a mixture of L and D forms. The corresponding amino acid may be a natural or an unnatural amino acid.

In a fourth broad aspect, there are provided compounds of Formula VI, or pharmaceutically acceptable salts or esters thereof, for use in the treatment and/or prevention of cerebrovascular diseases:

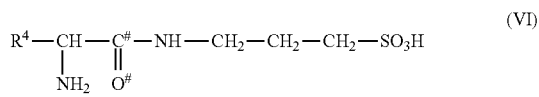

where $R^4$ is a side chain of a natural or unnatural amino acid; $O^\#$ is an oxygen atom of natural abundance, an $^{18}$O-enriched oxygen ($^{18}$O), an $^{17}$O-enriched oxygen ($^{17}$O) or a combination thereof; and $C^\#$ is a carbon atom of natural abundance, a $^{13}$C-enriched carbon or a combination thereof, provided that $O^\#$ and $C^\#$ are not both atoms of natural abundance (in other words, at least one of $O^\#$ and $C^\#$ is an isotope-enriched atom, i.e., at least one of $O^\#$ and $C^\#$ is not an atom of natural abundance). The corresponding amino acid may be an L-amino acid, a D-amino acid, or a mixture of L and D forms. The corresponding amino acid may be a natural or unnatural amino acid.

It should be understood that use of compounds in which all the atoms or elements in the structure are in their natural abundance (non-isotope enriched compounds) are not encompassed by the methods of the present invention.

In some embodiments, the compound of Formula (I), (III), (IV), (V), or (VI) is not N-acetyl-3-amino-1-propanesulfonic acid (also referred to herein as 3-(acetylamino)-1-propanesulfonic acid) or a salt or ester thereof.

In some embodiments, the compound of Formula (I), (II), (III), (IV), (V), or (VI) is not 3-amino-1-propanesulfonic acid (3APS) or a salt or ester thereof.

Compounds for use in the methods provided herein, e.g., compounds of Formula (I), (II), (III), (IV), (V), or (VI), may be enriched for one or more than one isotope. Any stable or pharmaceutically acceptable isotope may be used to enrich a compound for use in the methods of the disclosure. For example, an isotope-enriched compound may comprise D (2H), $^{13}$C, $^{15}$N, $^{17}$O, and/or $^{18}$O.

In some embodiments, isotope-enriched compounds for use in the methods provided herein, e.g., compounds of Formula (I), (II), (III), (IV), (V), or (VI), may be a compound shown in Table 1, Table 2, Table 3, or Table 4, or a pharmaceutically-acceptable salt, ester, chelator, hydrate, solvate, stereoisomer, or polymorphic form thereof.

In some embodiments, the present disclosure provides the use of a compound of general formula (I), (II), (III), (IV), (V) or (VI) for the treatment and/or prevention of cerebrovascular diseases that are not amyloid-β related. In some such embodiments, the cerebrovascular disease is stroke, e.g., hemorrhagic stroke or ischemic stroke, i.e., a non-amyloid-β related stroke, ischemia or hemorrhage. In some such embodiments, the cerebrovascular disease is vascular dementia, i.e., non-amyloid-β related vascular dementia.

It should be understood that cerebrovascular diseases according to the methods of the present invention do not include amyloid-β related diseases. Non-limiting examples of cerebrovascular diseases according to the methods of the present invention include non-amyloid-β related vascular dementia, multiple infarct dementia, single infarct dementia, hemorrhagic dementia, ischemic stroke, hemorrhagic stroke, subcortical vascular dementia, autosomal dominant arterial disease (CADASIL) with subcortical infarction and white matter encephalopathy, degenerative dementia, dementia caused by special partial infarction, mild cognitive impairment, large area cerebral infarct dementia, hereditary intracerebral hemorrhage, small vascular dementia, Binswanger's disease, dementia of mixed vascular and degenerative origin, dementia associated with Parkinson's disease, dementia associated with progressive supranuclear palsy, and dementia associated with cortical basal degeneration.

In one embodiment, there is provided the use of a compound of general formula (I), (II), (III), (IV), (V) or (VI) for the treatment and/or prevention of stroke (non-amyloid-β related). In an embodiment, the stroke is hemorrhagic stroke. In another embodiment, the stroke is ischemic stroke.

In one embodiment, there is provided the use of a compound of general formula (I), (II), (III), (IV), (V) or (VI) for the treatment and/or prevention of vascular dementia (non-amyloid-β related).

In another embodiment, there is provided the use of compounds of general formula (I), (II), (III), (IV), (V) or (VI) for the treatment and/or prevention of cognitive and/or behavioral disorders that are not amyloid-β related, particularly cognitive and/or behavioral disorders caused by cerebrovascular diseases such as hemorrhagic or ischemic stroke, global cerebral ischemia and hypoxia, and the like. Non-limiting examples of cognitive and/or behavioral disorders include vascular dementia, multiple infarct dementia, single infarct dementia, large area cerebral infarction dementia, dementia caused by special partial infarction, hemorrhagic dementia, subcortical vascular dementia, and small vascular dementia (such as, e.g., Binswanger's disease).

In some embodiments, the isotope-enriched compound of Formula (I), (II), (III), (IV), (V), or (VI) for use in accordance with the present disclosure is a compound shown in Table 1, Table 2, Table 3, or Table 4, or a pharmaceutically-acceptable salt, ester, chelator, hydrate, solvate, stereoisomer, or polymorphic form thereof:

TABLE 1

3,3-Dideuterium-3-amino-1-propanesulfonic acid, $^{15}$N-3-amino-1-propanesulfonic acid and selected derivatives.

| No. | Structure |
|---|---|
| 1 | H$_2$N-CD$_2$-CH$_2$-CH$_2$-SO$_3$H |
| 2 | Ala-NH-CD$_2$-CH$_2$-CH$_2$-SO$_3$H |
| 3 | Ser-NH-CD$_2$-CH$_2$-CH$_2$-SO$_3$H |
| 4 | Val-NH-CD$_2$-CH$_2$-CH$_2$-SO$_3$H |
| 5 | Phe-NH-CD$_2$-CH$_2$-CH$_2$-SO$_3$H |
| 6 | His-NH-CD$_2$-CH$_2$-CH$_2$-SO$_3$H |
| 7 | H$_2$$^{15}$N-CH$_2$CH$_2$CH$_2$-SO$_3$H |
| 8 | Ala-$^{15}$NH-CD$_2$-CH$_2$-CH$_2$-SO$_3$H |

TABLE 1-continued 3,3-Dideuterium-3-amino-1-propanesulfonic acid, $^{15}$N-3-amino-1-propanesulfonic acid and selected derivatives.

| No. | Structure |
|---|---|
| 9 | Ser-$^{15}$NH-CH$_2$CH$_2$CH$_2$-SO$_3$H |
| 10 | Val-$^{15}$NH-CH$_2$CH$_2$CH$_2$-SO$_3$H |
| 11 | Phe-$^{15}$NH-CH$_2$CH$_2$CH$_2$-SO$_3$H |
| 12 | His-$^{15}$NH-CH$_2$CH$_2$CH$_2$-SO$_3$H |

TABLE 2

Examples of N-($^{18}$O- and $^{17}$O-aminoacylated) 3-amino-1-propanesulfonic acid prodrugs.

| No. | Structure |
|---|---|
| 13 | Ala-C($^{18}$O)-NH-CH$_2$CH$_2$CH$_2$-SO$_3$H |
| 14 | Ser-C($^{18}$O)-NH-CH$_2$CH$_2$CH$_2$-SO$_3$H |
| 15 | Val-C($^{18}$O)-NH-CH$_2$CH$_2$CH$_2$-SO$_3$H |
| 16 | Phe-C($^{18}$O)-NH-CH$_2$CH$_2$CH$_2$-SO$_3$H |

TABLE 2-continued

Examples of N-($^{18}$O- and $^{17}$O-aminoacylated) 3-amino-1-propanesulfonic acid prodrugs.

| No. | Structure |
|---|---|
| 17 | Histidine derivative with $^{18}$O on carbonyl, amide-linked to propanesulfonic acid |
| 18 | Alanine derivative with $^{17}$O on carbonyl, amide-linked to propanesulfonic acid |
| 19 | Serine derivative with $^{17}$O on carbonyl, amide-linked to propanesulfonic acid |
| 20 | Valine derivative with $^{17}$O on carbonyl, amide-linked to propanesulfonic acid |
| 21 | Phenylalanine derivative with $^{17}$O on carbonyl, amide-linked to propanesulfonic acid |
| 22 | Histidine derivative with $^{17}$O on carbonyl, amide-linked to propanesulfonic acid |

TABLE 3

Examples of N-(1-$^{13}$C-aminoacyl)-3-amino-1-propanesulfonic acid prodrugs and selected isotope-enriched prodrugs.

| No. | Structure |
|---|---|
| 23 | Alanine derivative with $^{13}$C on carbonyl, amide-linked to propanesulfonic acid |
| 24 | Serine derivative with $^{13}$C on carbonyl, amide-linked to propanesulfonic acid |
| 25 | Valine derivative with $^{13}$C on carbonyl, amide-linked to propanesulfonic acid |
| 26 | Phenylalanine derivative with $^{13}$C on carbonyl, amide-linked to propanesulfonic acid |
| 27 | Histidine derivative with $^{13}$C on carbonyl, amide-linked to propanesulfonic acid |
| 28 | Valine derivative with $^{13}$C on carbonyl, amide-linked to $D_2$-propanesulfonic acid |
| 29 | Valine derivative with $^{18}$O on carbonyl, amide-linked to $D_2$-propanesulfonic acid |
| 30 | Valine derivative with $^{17}$O on carbonyl, amide-linked to $D_2$-propanesulfonic acid |
| 31 | Valine derivative with $^{18}$O and $^{13}$C on carbonyl, amide-linked to $D_2$-propanesulfonic acid |
| 32 | Valine derivative with $^{18}$O on carbonyl, $^{15}$N amide-linked to propanesulfonic acid |

TABLE 4

Examples of isotope-enriched 3-(cysteinylamino)-1-propanesulfonic acid.

| No. | Structure |
|---|---|
| 33 | Cysteine derivative amide-linked to $D_2$-propanesulfonic acid |
| 34 | Cysteine derivative with $^{15}$N amide linkage to propanesulfonic acid |

TABLE 4-continued

Examples of isotope-enriched 3-(cysteinylamino)-1-propanesulfonic acid.

| No. | Structure |
|---|---|
| 35 | 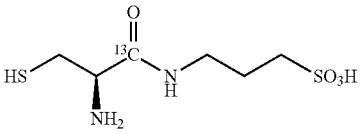 [SMILES: N[C@@H](CS)[13C](=O)NCCCS(=O)(=O)O] |
| 36 | 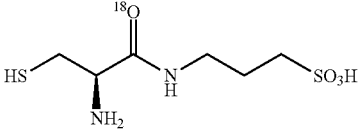 |
| 37 | 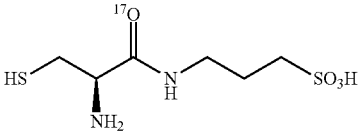 [SMILES: N[C@@H](CS)C(=[17O])NCCCS(=O)(=O)O] |
| 38 | 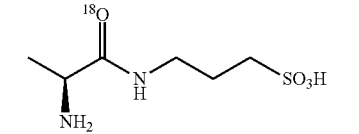 |
| 39 | 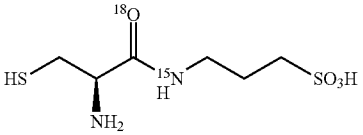 [SMILES: N[C@@H](CS)C(=[18O])[15NH]CCCS(=O)(=O)O] |
| 40 | 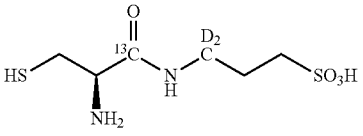 |
| 41 | 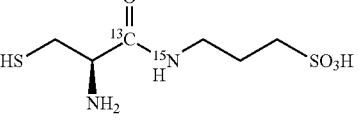 |
| 42 | 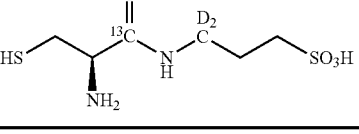 |

In an embodiment, the isotope-enriched compound is 3-(acylamino)-3,3-dideuterium-1-propanesulfonic acid or 3-(acyl($^{15}$N-amino))-1-propanesulfonic acid, where the acyl group is selected from arginyl, aspartyl, asparigyl, cystyl, glutamyl, glutaminyl, glycyl, isoleucyl, leucyl, lysyl, methionyl, prolyl, selenocystyl, threonyl, tryptophanyl, tyrosyl, and 4-hydroxyisoleucyl; or a pharmaceutically-acceptable salt, ester, chelator, hydrate, solvate, stereoisomer, or polymorphic form thereof.

In another embodiment, the isotope-enriched compound is 3-((1-$^{13}$C-acyl)amino)-1-propanesulfonic acid, 3-((1-$^{18}$O-acyl)amino)-1-propanesulfonic acid, or 3-((1-$^{17}$O-acyl) amino)-1-propanesulfonic acid, where the acyl group is selected from arginyl, aspartyl, asparigyl, cystyl, glutamyl, glutaminyl, glycyl, isoleucyl, leucyl, lysyl, methionyl, prolyl, selenocystyl, threonyl, tryptophanyl, tyrosyl, and 4-hydroxyisoleucyl; or a pharmaceutically-acceptable salt, ester, chelator, hydrate, solvate, stereoisomer, or polymorphic form thereof.

In some embodiments, the isotope-enriched compounds for use in the methods of the present invention are in their original acid or base forms (also referred to as "free form"), such as amino sulfonic acid. In other embodiments, the isotope-enriched compounds for use in the methods of the present invention encompass other pharmaceutically accepted forms or the original form, such as inorganic salt, organic salt, ester, chelator, hydrate, or solvate. The invention also encompasses use of different polymorphic forms of isotope-enriched compounds according to Formulae I to VI and Tables 1-4.

Without wishing to be limited by theory, it is believed that isotope-enriched derivatives and/or prodrugs of 3APS provided herein can improve therapeutic efficacy of 3APS by improving its therapeutic bio-distribution and/or pharmaco-kinetic profiles, for example by increasing bioavailability of the drug, reducing metabolism of the drug, increasing drug stability, and/or changing the release rate of drug from a prodrug.

In some embodiments of methods provided herein, the isotope-enriched compound is a compound of any one of Formulae (I)-(VI) as described herein, or a pharmaceutically acceptable salt thereof. In one embodiment of methods provided herein, the isotope-enriched compound is a compound of any one of Formulae (I)-(VI) as described herein, or a pharmaceutically acceptable salt thereof, wherein the compound is not N-acetyl-3-amino-1-propanesulfonic acid (also referred to herein as 3-(acetylamino)-1-propanesulfonic acid), or a pharmaceutically acceptable salt or ester thereof. In another embodiment of methods provided herein, the isotope-enriched compound is a compound of any one of Formulae (I)-(VI) as described herein, or a pharmaceutically acceptable salt thereof, wherein the compound is not 3-amino-1-propanesulfonic acid (3APS), or a pharmaceutically acceptable salt or ester thereof.

In some embodiments of methods provided herein, the isotope-enriched compound is 3-amino-3,3-dideuterium-1-propanesulfonic acid, or a pharmaceutically acceptable salt or ester thereof. In an embodiment, the isotope-enriched compound is 3-amino-3,3-dideuterium-1-propanesulfonic acid. In an embodiment, the isotope-enriched compound is a pharmaceutically acceptable salt of 3-amino-3,3-dideuterium-1-propanesulfonic acid, e.g., a sodium salt.

In some embodiments of methods provided herein, the isotope-enriched compound is 3-($^{15}$N-amino)-1-propanesulfonic acid, or a pharmaceutically acceptable salt or ester thereof. In an embodiment, the isotope-enriched compound is 3-($^{15}$N-amino)-1-propanesulfonic acid. In an embodiment, the isotope-enriched compound is a pharmaceutically acceptable salt of 3-($^{15}$N-amino)-1-propanesulfonic acid, e.g., a sodium salt.

In some embodiments of methods provided herein, the isotope-enriched compound is 3-((L-valyl)amino))-3,3-dideuterium-1-propanesulfonic acid, or a pharmaceutically acceptable salt or ester thereof. In an embodiment, the isotope-enriched compound is 3-((L-valyl)amino))-3,3-dideuterium-1-propanesulfonic acid. In an embodiment, the isotope-enriched compound is a pharmaceutically acceptable salt of 3-((L-valyl) amino))-3,3-dideuterium-1-propanesulfonic acid, e.g., a sodium salt.

In some embodiments of methods provided herein, the isotope-enriched compound is administered in the form of a pharmaceutical composition for use in the treatment or prevention of cerebrovascular disease, such as, without limitation, vascular dementia or stroke. In some embodiments, therefore, there is provided a method for treating or preventing cerebrovascular disease in a subject, the method comprising administering a pharmaceutical composition described herein, such that cerebrovascular disease is treated or prevented in the subject. In some embodiments, there is provided a method for treating or preventing stroke (non-amyloid-β related) in a subject, the method comprising administering a pharmaceutical composition described herein, such that stroke is treated or prevented in the subject. In some embodiments, there is provided a method for treating or preventing vascular dementia (non-amyloid-O related) in a subject, the method comprising administering a pharmaceutical composition described herein, such that vascular dementia is treated or prevented in the subject. In some embodiments, there is provided a method for treating or preventing cognitive decline (non-amyloid-β related) in a subject, the method comprising administering a pharmaceutical composition described herein, such that cognitive decline is treated or prevented in the subject. In some embodiments, there is provided a method for treating or preventing a cognitive and/or behavioral disorder (non-amyloid-β related, e.g., caused by a cerebrovascular disease) in a subject, the method comprising administering a pharmaceutical composition described herein, such that the cognitive and/or behavioral disorder is treated or prevented in the subject. Pharmaceutical compositions for use in the methods of the present disclosure generally comprise a compound of any one of Formulae (I)-(VI) or Tables 1-4 as described herein, or a pharmaceutically acceptable salt thereof, and a pharmaceutically acceptable carrier.

In some embodiments, isotope-enriched compounds and compositions for use in the methods of the present disclosure can act to increase the therapeutic effectiveness of the drug. In some embodiments, isotope-enriched compounds and compositions for use in the methods of the present disclosure can act to reduce the metabolism of the drug in a subject and/or to reduce the side effects of the drug in a subject.

In accordance with methods of the present disclosure, isotope-enriched compounds of Formulas I to VI and compositions thereof are provided for use to prevent and/or treat cerebrovascular disease, such as vascular dementia and/or stroke. In embodiments, the disclosure relates to treatment and/or prevention of cerebrovascular diseases that are not amyloid-β related, such as vascular dementia, stroke, cognitive decline caused by stroke, cognitive decline caused by global cerebral ischemia and hypoxia, and the like.

In some embodiments of methods of the invention, isotope-enriched compounds of Formulas I to VI and compositions thereof can treat and improve cognitive impairment and/or behavioral impairment caused by an ischemic or hemorrhagic cerebrovascular disease or global cerebral ischemia and/or hypoxia. Improvement in cognitive and/or behavioral impairment may be measured using art-recognized tests such as, without limitation, performance on a cognitive test, or behavioral performance such as learning, memory, thinking ability, insight, and the like. Non-limiting examples of tests for cognitive impairment include the Cognitive Abilities Screening Instrument (CASI) test, the Mini-Mental State Examination (MMSE), the Modified Mini-Mental State (3MS) examination, the Assessment Scale-Cognitive Subscale (ADAS-Cog-11), the VADAS-Cog (a variant of the ADAS-Cog adapted to assess people with vascular dementia, generally consisting of the standard ADAS-Cog with additional measures for attention, working memory, executive function, and verbal fluency), the Short Test of Mental Status (STMS), the General Practitioner Assessment of Cognition (GPCOG) test, the seven minute screen (7MS) test, the Abbreviated Mental Test (AMT), the Mini-Cog© test, the Six-Item Screener (SIS) test, the Six-Item Cognitive Impairment Test (6CIT), the Clock Drawing Test (CDT), the Time and Change (T&C) test, the Addenbrooke Cognitive Examination-Revised (ACE-R), the Memory Impairment Screen (MIS), and the DemTect® test.

As used herein, the terms "non-amyloid-β disease" and "non-amyloid-β related disease" are used interchangeably to refer to cerebrovascular diseases which are not amyloid-β related diseases, i.e., not characterized by abnormal accumulation of amyloid-β protein in the brain. Examples of non-amyloid-O cerebrovascular diseases include, without limitation, non-amyloid-β related vascular dementia, multiple infarct dementia, single infarct dementia, hemorrhagic dementia, ischemic stroke, hemorrhagic stroke, subcortical vascular dementia, autosomal dominant arterial disease (CADASIL) with subcortical infarction and white matter encephalopathy, degenerative dementia, dementia caused by special partial infarction, mild cognitive impairment, large area cerebral infarct dementia, hereditary intracerebral hemorrhage, small vascular dementia, Binswanger's disease, dementia of mixed vascular and degenerative origin, dementia associated with Parkinson's disease, dementia associated with progressive supranuclear palsy, or dementia associated with cortical basal degeneration.

In some embodiments of methods of the invention, isotope-enriched compounds of Formulas I to VI and compositions thereof can treat cognitive impairment, delay or slow the progression of cognitive impairment, or reduce the rate of decline of cognitive function, in a subject having or at risk of having cognitive impairment or decline of cognitive function, wherein the cognitive impairment or decline of cognitive function accompanies cerebrovascular disease, vascular dementia, stroke, global cerebral ischemia, or hypoxia and is not amyloid-β related.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
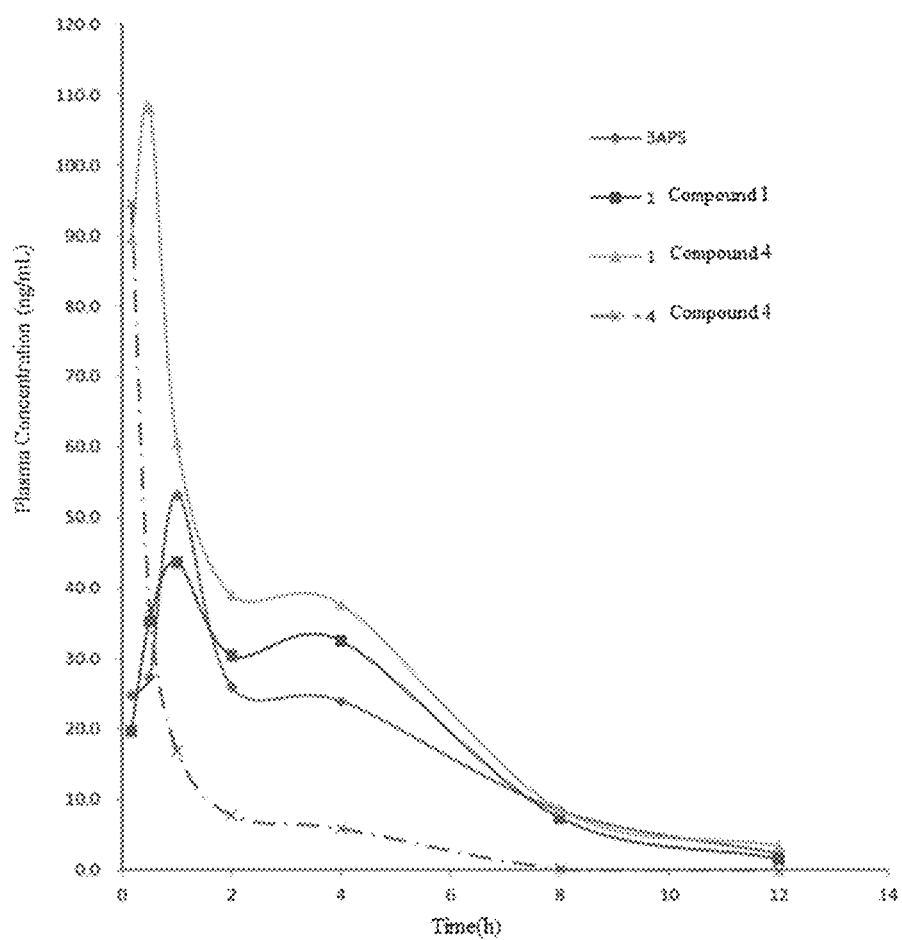
FIG. 1 shows plasma concentration-time curves of the compound following an oral administration of 3APS (non-isotope enriched), compound 1, and compound 4, including the concentration-time curve of compound 4 in the same experiment. Curves labeled with -♦-, -■-, and -▲- represent plasma drug concentration following administration of 3APS (of natural abundance), compound 1 and compound 4, respectively; and the curve labeled with -x- represents plasma prodrug concentration following administration of compound 4. The figure shows that at the mole-equivalent oral dose, the isotope-enriched compound 1 had a delayed metabolic profile and an improved exposure compared to 3APS, while compound 4 demonstrated even greater improvement of drug exposure. (Reproduced from U.S. Pat. No. 10,472,323 with permission.)

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used herein to indicate that a value includes an inherent variation of error for the device or the method being employed to determine the value.

The term "derivative" as used herein refers to a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "acyclic" refers to an organic moiety without a ring system. The term "aliphatic group" includes organic moieties characterized by straight or branched-chains, typically having between 1 and 15 carbon atoms. Aliphatic groups include non-cyclic alkyl groups, alkenyl groups, and alkynyl groups.

As used herein, the term "alkenyl" refers to unsaturated hydrocarbons having from two to twelve carbon atoms, including linear, branched, and cyclic non aromatic alkenyl groups, and comprising between one to six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, cyclopentenyl, cyclohexenyl, ethylcyclopentenyl, ethylcylohexenyl, and the like. The term alkenyl includes both unsubstituted alkenyl groups and substituted alkenyl groups. The term "$C_2$-$C_n$alkenyl", wherein n is an integer from 3 to 12, refers to an alkenyl group having from 2 to the indicated "n" number of carbon atoms.

As used herein, the term "alkynyl" refers to unsaturated hydrocarbons having from two to twelve carbon atoms, including linear, branched, and cyclic non aromatic alkynyl groups, and comprising between one to six carbon-carbon triple bonds. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl", wherein n is an integer from 3 to 12, refers to an alkynyl group having from 2 to the indicated "n" number of carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal or less than 8 carbon atoms in their ring structure.

The terms "aryl" and "aryl ring" refer to aromatic groups having "4n+2".pi.(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "4n+2".pi.(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a C1-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to an heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —NR$^a$R$^b$, in which Ra and R$^b$ are each independently hydrogen, alkyl, aryl, or heterocyclyl, or Ra and R$^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein means an amine group having respectively one and at least two $C_1$-$C_6$alkyl groups attached thereto. The term "arylamino" and "diarylamino" include groups wherein the nitrogen is bound to at least one or two aryl groups, respectively. The term "amide" or "aminocarbonyl" includes compounds or moieties which contain a nitrogen atom which is bound to the carbon of a carbonyl or a thiocarbonyl group. The term acylamino refers to an amino group directly attached to an acyl group as defined herein.

The term "nitro" means —NO$_2$; the terms "halo" and "halogen" refer to bromine, chlorine, fluorine or iodine substituents; the term "thiol", "thio", or "mercapto" means SH; and the term "hydroxyl" or "hydroxy" means —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" or "lower alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as perhalogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_6$alkyl, $C_1$-$C_6$alkenyl, $C_1$-$C_6$alkynyl, e.g., acetyl), a cycloalkyl group ($C_3$-$C_8$cycloalkyl), a heterocyclic group ($C_3$-$C_8$heterocycloalkyl and $C_5$-$C_6$heteroaryl), an aromatic group ($C_6$aryl, e.g., benzoyl), and the like. Acyl groups may be unsubstituted or substituted acyl groups (e.g. salicyloyl).

It should be understood that "substitution" or "substituted with" includes the implicit proviso that such substitution is in accordance with the permitted valence of the substituted atom and the substituent, and that the substitution results in a stable compound, i.e., a compound which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g., if the group contains an alkyl group, an aryl group, or other.

The term "unsubstituted" or "without substitution" refers to a compound or a group having no other substituent group except that the unidentified valence is chemically saturated with hydrogen atoms.

The term "solvate" refers to a physical association of a compound with one or more solvent molecules, whether organic or inorganic. This physical association includes hydrogen bonding. In certain instances, a solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, ethanolates, methanolates, hemiethanolates, and the like.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

As used herein, the term "cerebrovascular disease" refers to a variety of diseases related to cerebrovascular conditions, excluding those that are amyloid-β related (i.e., caused by, characterized by, or otherwise associated with abnormal accumulation of amyloid-β protein in the brain). Non-limiting examples of cerebrovascular disease in accordance with the methods of the present invention include non-amyloid-β related mild cognitive impairment (MCI), vascular dementia, multiple infarct dementia, single infarct dementia, hemorrhagic dementia, large area cerebral infarct dementia, dementia caused by special partial infarction, subcortical vascular dementia, small vascular dementia (such as Binswanger's disease), ischemic stroke, hemorrhagic stroke, autosomal dominant arterial disease (CADASIL) with subcortical infarction and white matter encephalopathy, hereditary intracerebral hemorrhage, degenerative dementia, dementia of mixed vascular and degenerative origin, dementia related to Parkinson's disease, dementia related to progressive supranuclear palsy, and dementia related to cortical basal degeneration.

As used herein, "AUC" refers to the area under a curve representing the concentration of a compound in a biological sample from a subject as a function of time following administration of the compound to the subject. Non-limiting examples of such biological samples include biological fluids such as plasma, blood, cerebrospinal fluid (CSF), and saliva; organ homogenates such as brain and liver homogenates; and the like. The AUC can be determined by measuring the concentration of a compound in a biological sample such as the plasma, blood, CSF or brain homogenate using methods such as liquid chromatography-tandem mass spectrometry (LC/MS/MS), at various time intervals, and calculating the area under the concentration-versus-time curve. Suitable methods for calculating the AUC from a drug concentration-versus-time curve are well known in the art. As relevant to the disclosure here, an AUC for 3APS can be determined by measuring the concentration of 3APS in the plasma, blood, CSF or brain homogenate of a subject following oral administration of a compound described herein to the subject.

"Bioavailability" refers to the rate and amount of a compound that reaches the systemic circulation of a subject following administration of the compound or a prodrug thereof to the subject and can be determined by evaluating, for example, the plasma or blood concentration-versus-time profile for the compound. Parameters useful in characterizing a plasma or blood concentration-versus-time curve include the area under the curve (AUC), the time to peak concentration ($T_{max}$), and the maximum compound concentration ($C_{max}$). "$C_{max}$" is the maximum concentration of a compound in the biological sample of a subject following administration of a dose of the compound to the subject. "$T_{max}$" is the time to the maximum concentration ($C_{max}$) of a compound in the biological sample of a subject following administration of a dose of the compound to the subject. Bioavailability is often expressed as F (%) referring to the ratio in percentage of the AUC of the compound for a specific mode of administration (e.g., orally) over AUC of the compound after intravenous (IV) administration.

"Bioequivalence" refers to equivalence of the rate and extent of absorption of a therapeutic agent, such as a compound, after administration of equal doses of the agent to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, or AUC.

As used herein the term "effective amount" refers to the amount or dose of a therapeutic agent, such as a compound, upon single or multiple dose administration to a subject, which provides the desired therapeutic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

As used herein, the term "therapeutic bio-distribution of 3APS" refers to one or more pharmacokinetic parameters of 3APS which affect 3APS therapeutic activity. Examples of such pharmacokinetic (PK) parameters include, but are not limited to: bioavailability of 3APS, AUC of 3APS, brain levels of 3APS, CSF levels of 3APS, $C_{max}$ of 3APS, $T_{max}$ of 3APS, and/or bio-absorption of 3APS, etc.

In some embodiments, therapeutic efficacy of a drug such as 3APS may be increased by increasing therapeutic bio-distribution of drug, e.g., increasing bioavailability of drug, increasing stability of drug, reducing metabolism of drug, and/or increasing other pharmacokinetic parameters of the drug after administration, as compared to administration of non-isotope enriched compound or drug or derivatives or prodrugs thereof.

As used herein, the terms "increased (or like terms, e.g., increasing, increase in, etc.) therapeutic effectiveness/efficacy of drug" (e.g., 3APS) and "enhanced (or like terms, e.g., enhancing, enhancement, etc.) therapeutic effectiveness/efficacy of drug" (e.g., 3APS) refer to an increased effectiveness of drug as measured, e.g., by one or more parameters listed under "therapeutic bio-distribution of drug" above, e.g., by 5%, 10%, 20%, 30%, 40%, 50%, 60%, 70%, 80%, 90%, 95%, 99%, 125%, etc., or even more, e.g., 2, or 4 fold, or even more when administered to a subject, e.g., animal or human, which increase is with respect to the same equivalent molar dose of non-isotope enriched drug or compound. In some embodiments, such % increases are achieved also with respect to 3APS administered orally in the formulation of Table 3 of U.S. Application Publication No. 2006-0079578, published Apr. 13, 2016. Effectiveness can also be as measured, for example, by effect on characteristics of a disease such as vascular dementia, e.g., by an improvement in selected manifestations of the disease, e.g., memory loss, cognition, reasoning, judgment, orientation, etc. Such effects may be measured using cognitive tests such as ADAS-COG, VADAS-COG, MMSE, CDR, and the like. Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function.

The term "lessening metabolism of 3APS" (or related terms such as reduction, less, lowering, reducing, lowered, etc) refers to decreasing the degree or amount of metabolism of 3APS, e.g., first-pass metabolism in the GI tract or liver of 3APS, by e.g., 5%, 10%, 20%, 30%, 40%, 50%, 60%, 70%, 80%, 90%, 95%, 99%, or even 100%, which decrease is with respect to the degree or amount of metabolism of 3APS that occurs when the same equivalent molar dose of non-isotope enriched 3APS is administered. In some embodiments, such % decreases may be achieved also with respect to 3APS administered orally in the formulation of Table 3 of U.S. Application Publication No. 2006-0079578, published Apr. 13, 2016.

The term "reduction of side effects of 3APS" refers to decreasing the amount of or severity of one or more side effects of 3APS by, e.g., 5%, 10%, 20%, 30%, 40%, 50%, 60%, 70%, 80%, 90%, 95%, 99%, or 99.9%, or even 100%, which decrease is with respect to the amount of or severity of a side effect of 3APS that is exhibited when the same equivalent molar dose of non-isotope enriched 3APS is administered. In some embodiments such % decreases are achieved also with respect to 3APS administered orally in the formulations of Table 3 of U.S. Application Publication No. 2006-0079578, published Apr. 13, 2016. More generally, the terms lessening etc., increasing etc., refer in context herein to the percentage changes, e.g., by 5%, 10%, 20%, 30%, 40%, 50%, 60%, 70%, 80%, 90%, 95%, 99%, 125%, etc., or even more, e.g., 2, or 4 fold, or even more.

In some embodiments, AUC of 3APS is increased by at least about 20% by administration of a compound of the present invention as compared to administration of the same equivalent molar dose of non-isotope enriched 3APS or a prodrug thereof. In some embodiments, oral AUC of 3APS is increased by at least about 20% by administration of a compound of the present invention as compared to oral administration of the same equivalent molar dose of non-isotope enriched 3APS or a prodrug thereof. In other embodiments, AUC is increased by at least about 5%, at least about 10%, at least about 25%, at least about 30%, or at least about 40%.

The contents of International Patent Application Publication No. WO2014026557 published on Feb. 20, 2014 are incorporated herein by reference in their entirety, including the data therein on cerebral infarction volume and behavioral score (such as the data in Tables 1 and 2 therein), especially for providing inter alia a comparative basis for the effects achieved by administration of compounds described herein.

The contents of U.S. Application Publication No. 2006-0079578, published Apr. 13, 2016, are incorporated herein by reference in their entirety, including the pharmacokinetic data therein (such as the data in Example 1 and Table 3 therein) for providing inter alia a comparative basis for the effects achieved by administration of compounds described herein.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, or carrier with which a compound is administered.

"Pharmaceutical composition" refers to at least one compound and at least one pharmaceutically acceptable vehicle, with which the compound is administered to a patient.

"Preventing" or "prevention" is intended to refer at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, DAD, VADAS-Cog, ADAS-Cog, or another test known in the art. For example, the methods of the invention may successfully treat a subject's dementia by slowing the rate of or lessening the extent of cognitive decline.

"Therapeutically effective amount" means the amount of compound that, when administered to a subject for treating or preventing a disease, is sufficient to effect such treatment or prevention of the disease. The "therapeutically effective amount" will vary depending on the compound, the disease and its severity, and the age, weight, etc., of the patient having the disease to be treated or prevented. As used herein, the term "therapeutically effective amount" refers to an amount of a compound or pharmaceutical composition sufficient to prevent, treat, inhibit, reduce, ameliorate or eliminate one or more causes, symptoms, or complications of a disease such as vascular dementia.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the bio-distribution (e.g., to allow agents which would not typically enter the reactive site of the protease) or the pharmacokinetics for a particular agent. A wide variety of groups have been used to modify compounds to form prodrugs, for example, esters, ethers, phosphates, etc. When the prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the parent drug.

The term "ester" refers to compounds that can be represented by the formula RCOOR (carboxylic ester) or the formula $RSO_3R'$ (sulfonate ester), where the group R can be, for example 3APS or the 3-aminopropane part thereof, and the group R' can be another organic group. These compounds are usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated or N-alkylated amino acids, as well as amino acids having nitrogen or oxygen-containing side chains (such as Lys, Cys, or Ser) in which the nitrogen or oxygen atom has been acylated or alkylated. Amino acids may be pure L or D isomers or mixtures of L and D isomers, including (but not limited to) racemic mixtures.

The term "natural amino acid" and equivalent expressions refer to L-amino acids commonly found in naturally-occurring proteins. Examples of natural amino acids include, without limitation, alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), (β-alanine (β-Ala), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), 2-aminopimelic acid (Apm), biphenylalanine (Bip), para-bromophenylalanine (4-Br-Phe), ortho-chlorophenylalanine (2-$C_1$-Phe), meta-chlorophenylalanine (3-Cl-Phe), para-chlorophenylalanine (4-$C_1$-Phe), meta-chlorotyrosine (3-$C_1$-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-$C_{1\text{-}2}$-Phe), 3,4-difluorophenylalanine (3,4-$F_2$-Phe), 3,5-diiodotyrosine (3,5-$I_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Ide), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

The term "side chain of an amino acid" refers to the side chain of a natural amino acid or an unnatural amino acid, as described hereinabove.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

Isotope-Enriched Compounds

Isotopic enrichment is a process by which the relative abundance of the isotopes of a given element are altered, thus producing a form of the element that has been enriched (i.e., increased) in one particular isotope and reduced or depleted in its other isotopic forms. As used herein, an "isotope-enriched" compound or derivative refers to a compound or derivative in which the level of an isotopic form of an atom or element has been increased relative to its natural abundance, i.e., one or more of the atoms or elements has been enriched (i.e., increased) in one or more isotopic form. Generally, in an isotope-enriched compound or derivative, the level of a specific isotopic form of an element at a specific position of the compound is increased. It should be understood however that the levels of isotopic forms of two or more elements in the compound may be increased. Further, an isotope-enriched compound may be a mixture of isotope-enriched forms that are enriched for more than one particular isotope, more than one element, or both. In some embodiments, an isotope-enriched compound is enriched isotopically with one or more isotopes of the same element. In some embodiments, an isotope-enriched compound is enriched isotopically with isotopes of one or more elements.

As used herein, the terms "element of natural abundance" and "atom of natural abundance" refer to an element or atom respectively of natural abundance, i.e., having the atomic mass most abundantly found in nature. By way of example, hydrogen of natural abundance is $^1H$ (protium); nitrogen of natural abundance is $^{14}N$; oxygen of natural abundance is $^{16}O$; carbon of natural abundance is $^{12}C$; and so on. As used herein, a "non-isotope enriched" compound is a compound in which all the atoms or elements in the compound are isotopes of natural abundance, i.e., all the atoms or elements have the atomic mass most abundantly found in nature. This is in contrast to an isotope-enriched compound in which one or more element is enriched for one or more specific isotopic form that is not the isotope of natural abundance. Non-isotope enriched compounds are excluded from compounds of the present invention and from use in methods of the invention provided herein.

Under normal conditions, the natural abundances for deuterium (D or $^2H$) (a stable isotope of hydrogen with a mass approximately twice that of the usual isotope), nitrogen-15 ($^{15}N$), carbon-13 ($^{13}C$), oxygen-18 ($^{18}O$), and oxygen-17 ($^{17}O$) are 0.016%, 0.37%, 1.11%, 0.204%, and 0.037%, respectively. By way of example, the term "oxygen of natural abundance" refers to an oxygen atom of natural isotope abundance, normally having the isotopic composition of oxygen atoms close to the Earth's atmosphere: $^{16}O$, 99.759%; $^{17}O$, 0.037%; and $^{18}O$, 0.204%. However, it should be understood that naturally occurring compounds may have slight variations in the isotopic composition of various elements.

An isotope-enriched compound or derivative possesses a level of an isotopic form of an atom or element that is higher than the natural abundance of that form. The level of isotope-enrichment will vary depending on the natural abundance of a specific isotopic form. As used herein, the expression "level of isotope-enrichment" means the amount or percentage of the compound that includes an isotopic form of an atom or element in place of the isotope of highest natural abundance. The terms "level of enrichment" and "%-enriched" are used interchangeably to refer to the amount or mole percentage of the compound that includes an isotopic form of an atom or element. For example, "95% $^{18}O$-enriched" means that 95 out of 100 (95/100) molecules have $^{18}O$-isotope, and 5/100 do not have $^{18}O$ but instead have other isotopic forms of oxygen ($^{17}O$ and/or $^{16}O$). Similarly, 95% $^{18}O$-enriched at a certain position/atom within the compound's structure means that 95/100 molecules have $^{18}O$ at that position/atom in the compound, whereas the other 5/100 have other isotopic forms of oxygen ($^{17}O$ and/or $^{16}O$) at that same position/atom.

In some embodiments, the level of isotope-enrichment for a compound, or for an element in a compound, may be from about 2 to about 100 molar percent (%), e.g., about 2%, about 5%, about 17%, about 30%, about 51%, about 83%, about 85%, greater than about 85%, about 90%, greater than about 90%, about 95%, greater than about 95%, about 96%, about 97%, about 98%, greater than about 98%, about 99%, greater than about 99%, or 100%. In one embodiment, the level of isotope-enrichment in an isotope-enriched compound of the invention (e.g., 3APS, a compound of any of Formulae (I)-(VI), etc.) is about 5% or higher, or about 10% or higher. In another embodiment, the level of isotope-enrichment in an isotope-enriched compound of the invention (e.g., 3APS, a compound of any of Formulae (I)-(VI), etc.) is about 20% or higher, or about 50% or higher. In yet another embodiment, the level of isotope-enrichment in an isotope-enriched compound of the invention (e.g., 3APS, a compound of any of Formulae (I)-(VI), etc.) is about 75% or higher, or about 90% or higher. In still another embodiment, the level of isotope-enrichment in an isotope-enriched compound of the invention (e.g., 3APS, a compound of any of Formulae (I)-(VI), etc.) is about 85% or higher. In still another embodiment, the level of isotope-enrichment in an isotope-enriched compound of the invention (e.g., 3APS, a compound of any of Formulae (I)-(VI), etc.) is about 90% or higher. In still another embodiment, the level of isotope-enrichment in an isotope-enriched compound of the invention (e.g., 3APS, a compound of any of Formulae (I)-(VI), etc.) is about 95% or higher. In another embodiment, the level of isotope-enrichment in an isotope-enriched compound of the invention (e.g., 3APS, a compound of any of Formulae (I)-(VI), etc.) is about 96% or higher. In another embodiment, the level of isotope-enrichment in an isotope-enriched compound of the invention (e.g., 3APS, a compound of any of Formulae (I)-(VI), etc.) is about 97% or higher. In another embodiment, the level of isotope-enrichment in an isotope-enriched compound of the invention (e.g., 3APS, a compound of any of Formulae (I)-(VI), etc.) is about 98% or higher. In another embodiment, the level of isotope-enrichment in an isotope-enriched compound of the invention (e.g., 3APS, a compound of any of Formulae (I)-(VI), etc.) is about 99% or higher. It should be understood that the level of isotope-enrichment for a particular compound, or a particular element of a compound, will be selected based on several properties of the compound such as its chemical, pharmacokinetic, and therapeutic profiles, with the aim of improving the compound's therapeutic efficacy, therapeutic bio-distribution, bioavailability, metabolism, stability, and/or pharmacokinetic profile. In some embodiments, the level of isotope-enrichment for a compound may be determined using mass spectrometry.

As used herein, the terms "Compounds of the present invention", "Compounds of the invention", "Compounds for use in the methods of the invention" and equivalent expressions are used interchangeably to refer to isotope-enriched compounds described herein as being useful in the methods of the invention, e.g., those encompassed by structural Formulae such as (I), (II), (III), (IV), (V), and (VI), and includes specific compounds mentioned herein such as those in Tables 1-4 as well as their pharmaceutically acceptable salts, esters, chelates, hydrates, and solvates.

Embodiments herein may exclude one or more of the compounds of the invention. In some embodiments, N-acetyl-3-amino-1-propanesulfonic acid and salts and esters thereof are excluded from compounds of the invention. In some embodiments, 3-amino-1-propanesulfonic acid (3APS) and salts and esters thereof are excluded from compounds of the invention.

As would be understood by a person of ordinary skill in the art, the recitation of "a compound" is intended to include salts, esters, solvates, hydrates, oxides, and inclusion complexes of that compound as well as any stereoisomeric form or polymorphic form, or a mixture of any such forms of that compound in any ratio. Thus, in accordance with some embodiments of the invention, a compound as described herein, including in the contexts of pharmaceutical compositions and methods of treatment is provided as the salt form.

It should be understood that compounds described herein for use in the methods of the invention may contain one or more chiral centers and/or double bonds and therefore, may exist as stereoisomers, such as double-bond isomers (i.e., geometric isomers), enantiomers, or diastereomers. Chemical structures disclosed herein are intended to encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. The chemical structures depicted herein are also intended to encompass all possible tautomeric forms of the illustrated compounds.

Compounds may exist in unsolvated forms as well as solvated forms, including hydrated forms. In general, compounds may be hydrated or solvated. Certain compounds may exist in multiple crystalline or amorphous forms. In general, all physical forms are intended to be encompassed herein.

The term "3APS" is used herein to refer to 3-amino-1-propanesulfonic acid, which is also known by alternate names including tramiprosate, Alzhemed™, and homotaurine. The terms "3APS of natural abundance" and "non-isotope enriched 3APS" refer specifically to 3APS in which all the atoms or elements in the structure are in their natural abundance (i.e., CAS RN 3687-18-1). The term "isotope-enriched 3APS" refers specifically to 3APS containing one or more isotope-enriched elements or atoms. The term "isotope-enriched 3APS derivatives and/or prodrugs" refers to a compound having at least one atom or element in its isotope-enriched form, either in the 3APS portion or in the protecting group portion, or in both.

Compounds described herein include, but are not limited to, their optical isomers, racemates, and other mixtures thereof. In those situations, the single enantiomers or diastereomer, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E- forms (or cis- and trans- forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

Pharmaceutical Compositions

In an embodiment, there is provided a pharmaceutical composition comprising a compound of the invention, e.g., a compound of any one of Formulae (I)-(VI), or a pharmaceutically acceptable salt, ester, or solvate thereof, and a pharmaceutically acceptable carrier, for use in the methods of the present disclosure. In an embodiment, there is provided a pharmaceutical composition comprising a compound in any one of Tables 1-4, or a pharmaceutically acceptable salt thereof, and a pharmaceutically acceptable carrier, for use in the methods of the present disclosure. In another embodiment, there is provided a pharmaceutical composition comprising a compound of any one of Formulae (I)-(VI) or a compound in any one of Tables 1-4, or a pharmaceutically acceptable salt thereof, and a pharmaceutically acceptable carrier, for use in the methods of the present disclosure, with the proviso that the compound is not N-acetyl-3-amino-1-propanesulfonic acid or a salt or ester thereof or 3-amino-1-propanesulfonic acid (3APS) or a salt or ester thereof.

The preparation of pharmaceutical compositions can be carried out as known in the art (see, for example, Remington: The Science and Practice of Pharmacy, 20$^{th}$ Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of a subject, e.g., humans and animals, without undue toxicity, irritation, allergic response, and the like, and are commensurate with a reasonable benefit/risk ratio.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated. Supplementary active compounds can also be incorporated into the compositions. For example, a pharmaceutical composition provided herein may further comprise at least one additional Alzheimer's disease therapeutic, as discussed below.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

In some embodiments, pharmaceutical compositions provided herein are suitable for oral administration. For example, a pharmaceutical composition may be in the form of a hard shell gelatin capsule, a soft shell gelatin capsule, a cachet, a pill, a tablet, a lozenge, a powder, a granule, a pellet, a pastille, or a dragee. Alternatively, a pharmaceutical composition may be in the form of a solution, an aqueous liquid suspension, a non-aqueous liquid suspension, an oil-in-water liquid emulsion, a water-in-oil liquid emulsion, an elixir, or a syrup. Pharmaceutical compositions may or may not be enteric coated. In some embodiments, pharmaceutical compositions are formulated for controlled release, such as delayed or extended release.

In further embodiments, compounds and compositions thereof may be formulated in multi-dose forms, i.e., in the form of multi-particulate dosage forms (e.g., hard gelatin capsules or conventional tablets prepared using a rotary tablet press) comprising one or more bead or minitab populations for oral administration. The conventional tablets rapidly disperse on entry into the stomach. The one or more coated bead or minitab populations may be compressed together with appropriate excipients into tablets (for example, a binder, a diluent/filler, and a disintegrant for conventional tablets.

Tablets, pills, beads, or minitabs of the compounds and compositions of the compounds may be coated or otherwise compounded to provide a dosage form affording the advantage of controlled release, including delayed or extended release, or to protect from the acid conditions of the stomach. For example, the tablet or pill can include an inner dosage and an outer dosage component, the latter being in the form of a coating over the former. The two components can be separated by a polymer layer that controls the release of the inner dosage.

In certain embodiments, the layer may comprise at least one enteric polymer. In further embodiments, the layer may comprise at least one enteric polymer in combination with at least one water-insoluble polymer. In still further embodiments, the layer may comprise at least one enteric polymer in combination with at least one water-soluble polymer. In yet further embodiments, the layer may comprise at least one enteric polymer in combination with a pore-former.

In certain embodiments, the layer may comprise at least one water-insoluble polymer. In still further embodiments, the layer may comprise at least one water-insoluble polymer in combination with at least one water-soluble polymer. In yet further embodiments, the layer may comprise at least one water-insoluble polymer in combination with a pore-former.

Representative examples of water-soluble polymers include polyvinylpyrrolidone (PVP), hydroxypropyl methylcellulose (HPMC), hydroxypropylcellulose (HPC), polyethylene glycol, and the like.

Representative examples of enteric polymers include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit (LI 00, S I 00, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of useful water-insoluble polymers include ethylcellulose, polyvinyl acetate (for example, Kollicoat SR #30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Any of the above polymers may be further plasticized with one or more pharmaceutically acceptable plasticizers. Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating an active compound, such as a compound of Formulae (I)-(VI) provided herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the prevention or treatment of a cerebrovascular disease. Dosages are discussed further below.

In some embodiments, there are provided pharmaceutical compositions that comprise a therapeutically effective amount of an isotope-enriched compound described herein, and a pharmaceutically acceptable carrier, for preventing or treating a cardiovascular disease. In one embodiment, there are provided pharmaceutical compositions that comprise a therapeutically effective amount of an isotope-enriched compound described herein, and a pharmaceutically acceptable carrier, for preventing or treating stroke. In one embodiment, there are provided pharmaceutical compositions that comprise a therapeutically effective amount of an isotope-enriched compound described herein, and a pharmaceutically acceptable carrier, for preventing or treating vascular dementia. In one embodiment, there are provided pharmaceutical compositions that comprise a therapeutically effective amount of an isotope-enriched compound described herein, and a pharmaceutically acceptable carrier, for preventing or treating cognitive and/or behavioral disorders caused by a cerebrovascular disease.

Methods of Use of Compounds and Compositions

The present disclosure relates to a method for preventing or treating cerebrovascular diseases by administering an effective dose of a compound or composition described herein to a subject in need thereof. Specifically, in some embodiments, there are provided methods for the prevention or treatment of cognitive and/or behavioral disorders caused by ischemic or hemorrhagic cerebrovascular diseases, global cerebral ischemia and/or hypoxia, such as, without limitation: vascular dementia, e.g., multiple infarct dementia, single infarct dementia, large area cerebral infarct dementia, dementia caused by special partial infarction, hemorrhagic dementia, subcortical vascular dementia, or small vascular dementia (such as Binswanger's disease); and the like.

Vascular dementia is a heterogeneous group of brain disorders in which cognitive impairment is attributable to cerebrovascular pathologies and is responsible for at least 20% of cases of dementia, being second only to Alzheimer's disease (AD) (Gorelick et al., Stroke, 2011; 42:2672-2713). Recent clinical-pathological studies have highlighted the role of cerebrovascular disease, not only as a primary cause of cognitive impairment, but also as an adjuvant to the expression of dementia caused by other factors, including other neurodegenerative pathologies (Gorelick et al., Stroke, 2011; 42:2672-2713; Schneider et. al., Neurology, 2007; 69:2197-2204; Toledo et al., Brain, 2013; 136:2697-2706). At the same time, new experimental findings have revealed a previously unrecognized functional and pathogenic synergy between neurons, glia and vascular cells (Iadecola, C., Acta Neuropathol. 2010; 120:287-296; Quaegebeur et al., Neuron, 2011; 71:406-424; Zlokovic, BV, Nat Rev Neurosci., 2011; 12:723-738), providing a new framework to reevaluate how alterations in cerebral blood vessels could contribute to the neuronal dysfunction underlying cognitive impairment. These advances highlight the role of vascular factors in cognitive health.

As used herein, "vascular dementia (VD)" refers to severe cognitive dysfunction syndrome caused by cerebrovascular disease. Causes of cognitive impairment related to vascular factors include, without limitation: hypoperfusion dementia; multiinfarct dementia; white matter lesions (Leukoaraiosis); small vessel disease; lacunar infarcts; microinfarcts; microbleeds; hemorrhages; CADASIL; post-stroke dementia; increased blood-brain-barrier (BBB) permeability; (for review, see Iadecola, C., The pathobiology of vascular dementia, Neuron. 2013 Nov. 20; 80(4): 10.1016/j.neuron.2013.10.008, doi: 10.1016/j.neuron.2013.10.008).

In the context of the present disclosure, the term "cerebrovascular diseases" excludes amyloid-β related diseases. The terms "Abeta", "Aβ", "β-amyloid", and "amyloid-β" are used interchangeably herein to refer to any peptide resulting from beta-secretase mediated cleavage of Amyloid Precursor Protein (APP), including for example peptides of 37, 38, 39, 40, 41, 42, and 43 amino acids, and extending from the beta-secretase cleavage site to amino acids 37, 38, 39, 40, 41, 42, or 43. As used herein, the terms "amyloid-β disease" and "amyloid-β related disease" refer to diseases and conditions whose etiology relates to amyloid-β accumulation in the brain. Such diseases and conditions are generally characterized by abnormal accumulation of amyloid-β protein in the brain as determined using standard methods such as, for example, imaging (e.g., positron emission tomography (PET) scan, magnetic resonance imaging (MRI)), measurement of amyloid-β levels in a sample from a subject (e.g., in cerebrospinal fluid (CSF), blood), measurement of biomarkers, and the like. Abnormal accumulation of amyloid-β may result from increased production, increased deposition, and/or reduced clearance of amyloid-β from the brain. It should be understood that some diseases can have diverse etiologies; for example, vascular dementia can be amyloid-β related or non-amyloid-β related (e.g., caused by a cerebrovascular disease such as stroke in the absence of amyloid-β accumulation). In such cases, the amyloid-β related form of the disease or condition is excluded from the methods of the invention. Specifically, methods provided herein are intended to encompass non-amyloid-β related-vascular dementia and exclude amyloid-β related-vascular dementia. Similarly, methods of the invention encompass non-amyloid-β related stroke, hemorrhage, dementia, cognitive decline, etc., and exclude amyloid-β related disorders such as Alzheimer's disease, CAA, hereditary cerebral hemorrhage, etc.

In an embodiment, there is provided a method for preventing or treating vascular dementia (non-amyloid-β related) by administering an effective dose of a compound or composition described herein to a subject in need thereof.

In an embodiment, there is provided a method for preventing or treating stroke (non-amyloid-β related) by administering an effective dose of a compound or composition described herein to a subject in need thereof. Stroke may be ischemic or hemorrhagic.

In an embodiment, there is provided a method for preventing or treating hemorrhage (non-amyloid-β related) by administering an effective dose of a compound or composition described herein to a subject in need thereof.

In an embodiment, there is provided a method for preventing or treating cognitive decline caused by stroke (non-amyloid-β related) by administering an effective dose of a compound or composition described herein to a subject in need thereof.

In an embodiment, there is provided a method for preventing or treating cognitive decline (non-amyloid-β related) caused by a cerebrovascular disease by administering an effective dose of a compound or composition described herein to a subject in need thereof.

In an embodiment, there is provided a method for preventing or treating a cognitive and/or behavioral disorder in a subject in need thereof, the method comprising administering to the subject a therapeutically effective amount of a compound or composition as described herein to the subject, wherein the cognitive and/or behavioral disorder is caused by a cerebrovascular disease or accident, a stroke, global cerebral ischemia, and/or hypoxia.

In an embodiment, there is provided a method for preventing or treating cognitive impairment, for delaying or slowing the progression of cognitive impairment, or for reducing the rate of decline of cognitive function, in a subject having or at risk of having cognitive impairment or decline of cognitive function, the method comprising administering to the subject a therapeutically effective amount of a compound or composition as described herein, wherein the cognitive impairment or decline of cognitive function accompanies and/or is caused by cerebrovascular disease, vascular dementia, stroke, global cerebral ischemia, or hypoxia and is not amyloid-β related.

In embodiments of methods provided herein, the cerebrovascular disease is not amyloid-β related.

"Cognitive function" refers to any higher order intellectual brain process or brain state involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care, speed of processing, reasoning and problem solving and social cognition.

Cognitive function may be measured, for example and without limitation, by the clinical global impression of change scale (CIBIC-plus scale); the Mini Mental State Exam (MMSE); the VADAS-Cog test; the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test; the explicit 3-alternative forced choice task, or MATRICS consensus neuropsychological test battery which includes tests of working memory, speed of processing, attention, verbal learning, visual learning, reasoning and problem solving and social cognition; or other cognitive tests described herein or known in the art. See Folstein et al., J Psychiatric Res 12: 189-98, (1975); Robbins et al., Dementia 5: 266-81, (1994); Rey, L'examen clinique en psychologie, (1964); Kluger et al., J Geriatr Psychiatry Neurol 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011), The FDA-NIMH-MATRICS guidelines for clinical trial design of cognitive-enhancing drugs: what do we know 5 years later? Schizophr. Bull. 37, 1209-1217.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function.

In addition to assessing cognitive performance, the progression of cognitive impairment and dementia may be monitored by assessing surrogate changes in the brain of the subject. Surrogate changes include, without limitation, changes in regional brain volumes, perforant path degradation, and changes seen in brain function through resting state fMRI (R-fMRI) and fluorodeoxyglucose positron emission tomography (FDG-PET). Examples of regional brain volumes useful in monitoring the progression of cognitive impairment and dementia include reduction of hippocampal volume and reduction in volume or thickness of entorhinal cortex and cerebral infarction volume. These volumes may be measured in a subject by, for example, MRI. See Aisen et al., Alzheimer's & Dementia 6:239-246 (2010). Resting-state fMRI (R-fMRI) involves imaging the brain during rest and recording large-amplitude spontaneous low-frequency (<0.1 Hz) fluctuations in the fMRI signal that are temporally correlated across functionally related areas. Seed-based functional connectivity, independent component analyses, and/or frequency-domain analyses of the signals are used to reveal functional connectivity between brain areas, as well as the extent of cognitive impairment and/or dementia. FDG-PET uses the uptake of FDG as a measure of regional metabolic activity in the brain. Decline of FDG uptake in regions such as the posterior cingulated cortex, temporoparietal cortex, and prefrontal association cortex has been shown to relate to the extent of cognitive decline and dementia. See Aisen et al., Alzheimer's & Dementia 6:239-246 (2010), Herholz et al., NeuroImage 17:302-316 (2002).

"Improving" cognitive function refers to affecting impaired cognitive function so that it more closely resembles the function of a normal, unimpaired subject. Cognitive function may be improved to any detectable degree. In an embodiment, cognitive function is improved sufficiently to allow an impaired subject to carry out daily activities of normal life at an improved level of proficiency, ideally as close as possible to a normal, unimpaired subject or an age-matched normal, unimpaired subject. In some embodiments, cognitive function of a subject may be improved to any detectable degree, as measured using one or more test such as a cognitive test, imaging, etc.

"Preserving" cognitive function refers to affecting normal or impaired cognitive function such that it does not decline or does not fall below that observed in the subject upon first presentation or diagnosis, or delaying such decline.

In some embodiments, treating cognitive decline includes improving and/or preserving cognitive function in a subject.

"Cognitive impairment" refers to cognitive function in subjects that is not as robust as that expected in a normal, unimpaired subject. In some cases, cognitive function is reduced by about 5%, about 10%, about 30%, about 40%, about 50% or more, compared to cognitive function expected in a normal, unimpaired subject. In some cases, "cognitive impairment" in subjects affected by a cerebrovascular disease or accident refers to cognitive function in subjects that is not as robust as that expected in an aged-matched normal, unimpaired subject (e.g., subjects with mean scores for a given age in a cognitive test).

"Behavioral impairment" refers to behavioral and psychological symptoms of dementia (BPSD), also known as neuropsychiatric symptoms, and includes a heterogeneous group of non-cognitive symptoms and behaviors occurring in subjects with dementia. BPSD are as clinically relevant as cognitive symptoms, as they strongly correlate with the degree of functional and cognitive impairment in a subject. Common BPSD can include, without limitation, agitation, anxiety, irritability, illusion and delusions, apathy, depression, disinhibition, aberrant motor and obsessive-compulsive behaviors, and sleep disorders, among others. These manifestations can be present at any stage of cognitive impairment and/or dementia. In some case, BPSD may be the first indication of change in a subject, before the occurrence of cognitive symptoms. See, e.g., Dillon, C. et al., Neuropsychiatr Dis Treat. 2013; 9: 1443-1455.

Behavioral impairment may be measured, for example and without limitation, using the Behavioral Pathology in Alzheimer's Disease Rating Scale (BEHAVE-AD), the Neurobehavioral Rating Scale, the Behavioral Rating Scale for Dementia, the Neuropsychiatric Inventory (NPI) or the NPI-Clinician (NPI-C). The NPI is one of the most widely used scales to measure behavioral impairment associated with cognitive disorders. It is a fully structured interview, which obtains data from an informant, usually the patient's caregiver. Other tests that may be used to evaluate behavioral impairment include, for example and without limitation, the Hamilton Depression Rating Scale, the Cornell Scale for Depression in Dementia, the Geriatric Depression Scale, or the Cohen-Mansfield Agitation Inventory.

The term "subject" includes living organisms with a cerebrovascular disease, or who are susceptible to or at risk of a cerebrovascular disease. Examples of subjects include humans, monkeys, cows, rabbits, sheep, goats, pigs, dogs, cats, rats, mice, and transgenic species thereof. The term "subject" generally includes animals susceptible to states characterized by a cerebrovascular disease, e.g., mammals, e.g. primates, e.g. humans. The animal can also be an animal model for a disorder, e.g., a transgenic mouse model, and the like. In one embodiment, the subject is a human.

In some embodiments, a subject is in need of treatment by the methods provided herein, and is selected for treatment based on this need. A subject in need of treatment is art-recognized, and includes subjects that have been identified as having a cerebrovascular disease or condition, or having a symptom of such a disease or condition, or being at risk of such a disease or condition (e.g., a subject having or at risk of having vascular dementia, stroke, cognitive decline caused by stroke, cognitive or behavioral impairment, etc.), and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

In some embodiments, the subject is a patient with vascular dementia (VD). In some embodiments, the VD is caused by stroke, e.g., an ischemic or hemorrhagic stroke.

In some embodiments, the subject is a patient with cognitive decline caused by stroke, e.g., an ischemic or hemorrhagic stroke.

In some embodiments, the subject is a patient who has or is at risk of having cognitive impairment or decline of cognitive function, wherein the cognitive impairment or decline of cognitive function accompanies or is caused by cerebrovascular disease, vascular dementia, stroke, global cerebral ischemia, or hypoxia and is not amyloid-β related.

In some embodiments, after administration of a compound or composition to a subject in need thereof, measurable differences (e.g., in scores on a cognitive test) can be observed between treated subject(s) and a placebo group or historical control group.

It should be understood that the dosage or amount of a compound and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens may depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a compound or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined as known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in compositions and methods provided herein. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg, about 250 mg, or about 500 mg and, for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound (e.g., of Formula I, Formula II, Formula III, Formula IV, Formula V, or Formula VI) which is effective at such dosage or as a multiple of the same, for instance, units containing 5 mg to 500 mg, usually around 10 mg to 200 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a compound described herein.

In some embodiments, the dosage range for oral administration is generally about 0.001 mg to about 2000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

In further embodiments, the dose is about 10 mg to about 1000 mg, including all ranges and subranges there between, e.g., about 10 mg to about 900 mg, about 10 mg to about 800 mg, about 10 to about 700 mg, about 10 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 900 mg, about 50 mg to about 800 mg, about 50 to about 700 mg, about 50 mg to about 600 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 900 mg, about 100 mg to about 800 mg, about 100 to about 700 mg, about 100 mg to about 600 mg, about 100 mg to about 500 mg, about 100 mg to about 400 mg, about 100 mg to about 300 mg, about 100 mg to about 250 mg, about 100 mg to about 200 mg, about 100 mg to about 150 mg, about 150 mg to about 200 mg, about 150 mg to about 250 mg, about 150 to about 300 mg, about 150 mg to about 400 mg, about 150 mg to about 500 mg, about 200 mg to about 900 mg, about 200 mg to about 800 mg, about 200 to about 700 mg, about 200 mg to about 500 mg, about 200 mg to about 400 mg, about 200 mg to about 300 mg, about 200 mg to about 250 mg, about 300 mg to about 900 mg, about 300 mg to about 800 mg, about 300 to about 700 mg, about 300 to about 600 mg, about 300 mg to about 500 mg, about 300 mg to about 400 mg, about 400 mg to about 900 mg, about 400 mg to about 800 mg, about 400 to about 700 mg, about 400 to about 600 mg, about 400 mg to about 500 mg, about 500 mg to about 900 mg, about 500 mg to about 800 mg, about 500 to about 700 mg, about 500 mg to about 600 mg, about 100 mg to about 500 mg, about 100 mg to about 400 mg, about 100 mg to about 300 mg, or about 100 mg to about 250 mg. In an embodiment, the range is about 150 mg to about 400 mg.

In still further embodiments, the dose is 10 mg, 25 mg, 50 mg, 60 mg, 70 mg, 75 mg, 80 mg, 85 mg, 90 mg, 100 mg, 105 mg, 110 mg, 115 mg, 120 mg, 125 mg, 130 mg, 135 mg, 140 mg, 145 mg, 150 mg, 160 mg, 170 mg, 180 mg, 190 mg, 200 mg, 225 mg, 250 mg, 265 mg, 275 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg. In an embodiment, the dose is 200 mg or higher. In an embodiment, the dose is 250 mg or higher. In an embodiment, the dose is between 200 mg and 300 mg. In an embodiment, the dose is between 250 mg and 300 mg. In an embodiment, the dose is 250 mg. In an embodiment, the dose is 265 mg. In an embodiment, the dose is 280 mg.

Administration of compounds and compositions provided herein can be carried out using known procedures, at dosages and for periods of time effective to achieve a desired purpose. Dosage regimens can be adjusted to provide the optimum therapeutic response. For example, several divided doses may be administered daily or the dose may be proportionally reduced as indicated by the exigencies of the therapeutic situation. Generally, a compound or composition can be administered by any suitable route or method, such as but not limited to oral, parenteral, intravenous, intraperitoneal, intramuscular, sublingual, local or intranasal administration, inhalation and other methods commonly used in the art.

In some embodiments, therapeutic efficacy of methods of the disclosure may be determined by using cognitive tests known in the art, such as, for example and without limitation, VaDAS-cog (vascular dementia evaluation scale). VaDAS-cog helps evaluate cognition and differentiates between normal cognitive functioning and impaired cognitive functioning. The VaDAS-cog can be used in clinical trials in order to determine incremental improvements or declines in cognitive functioning. For example, an increased VaDAS-cog score compared to placebo can indicate improved cognitive functioning.

In methods provided herein, compounds and compositions described herein may be administered once, twice, three, or four times daily, using any suitable mode described above. Also, in certain embodiments, administration or treatment with the compounds according to any of the formulae described herein may be continued for a number of weeks; for example, commonly treatment would continue for at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, or 104 weeks. In yet further embodiments, administration or treatment with compounds according to any of the formulae described herein and compositions thereof may be continued for a number of months; for example, commonly treatment would continue for at least 2 months, 4 months, 6 months, 8 months, 10 months, 12 months, 15 months, 18 months, 20 months, or 24 months. In still further embodiments, administration or treatment with the compounds according to any of the formulae described herein and compositions thereof may be continued indefinitely. In still further embodiments, administration or treatment with the compounds according to any of the formulae described herein and compositions thereof may be continued until the VaDAS-cog score improves by about 1.5-fold to about 4.5-fold. In some embodiments, the VaDAS-cog score is improved by about 1.5-fold, about 2.0-fold, about 3.5-fold, about 4.0-fold, about 4.5-fold, about 5.0-fold, about 7.5-fold, about 10.0-fold, about 15.0-fold with the methods provided herein. In one embodiment, the VaDAS-cog score is improved by about 1.5-fold to about 10.0-fold.

It should be understood that in the methods provided herein, the compounds and/or compositions described herein may be used alone or in combination with other therapies. Non-limiting examples of other therapies for cerebrovascular diseases include cognitive enhancers (such as acetylcholinesterase inhibitors, NMDA receptor antagonists, etc.), muscle relaxants, diuretics, antihypertensives, and the like. The latter can be administered before, after or simultaneously with the application of the compounds and/or compositions described herein. U.S. Patent Application Publication No. 2014-0080873, which is incorporated herein by reference, provides a list of exemplary "therapeutic drugs" that can be used in combination with the compounds and compositions described herein. Drugs that can be used with compounds and compositions described herein to prevent or treat vascular dementia or its symptoms may include, but are not limited to, baclofen and/or torasemide. Methods provided herein could also comprise administration of vaccines and/or antibodies for the prevention or treatment of cerebrovascular disease such as vascular dementia.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

General Methods for Preparation and Use of Compounds of the Invention.

General Method A. Preparation and use of 3-amino-1-propanesulfonic acid (3APS) sodium salt. 3APS of natural abundance or isotope-enriched 3APS was dissolved in water, followed by addition of 1 molar equivalent of sodium hydroxide. The mixture was kept at room temperature (r.t.) for 10 min., concentrated to dryness, and further dried under vacuum. The solid residue was sodium salt of 3APS, which was used in the following synthesis without purification.

General Method B. De-salting using ion-exchange resin. Crude product containing sodium chloride or sodium bromide (e.g., 2 mmol) was dissolved in water (e.g., 10 mL), followed by addition of Amberlite IR-120 (H-form) (2 mL). The mixture was stirred for 3 min. and filtered. The resin was washed with water (e.g., 2 mL x 3). The filtrate and washings were combined and treated with resin once more. An optional third treatment with resin was done if there was chloride or bromide ion remaining in the solution. The aqueous solution thus obtained was concentrated to dryness (rotary evaporator), and further dried to give salt-free product.

Example 1. Synthesis of 3-amino-3,3-dideuterium-1-propanesulfonic Acid (1) and sodium 3-amino-3,3-dideuterium-1-propanesulfonate (1s)

3-Hydroxypropanenitrile (26.0 g, 366 mmol, 1.0 eq.) was dissolved in dry THF (50 mL). The solution was added dropwise to a stirring suspension of LiAlD4 (10.0 g, 238 mmol, 0.65 eq.) in dry THF (200 mL). After heating at reflux overnight, the reaction mixture was hydrolyzed at r.t. by slow addition of water (4.8 mL), 15% NaOH solution (4.8 mL), and water (14.4 mL) subsequently. The mixture was stirred for 2 hours (h) and filtered under reduced pressure. The organic phase from the filtration was evaporated to dryness, giving a red oil material, which was used in the next step without purification.

The oil material (10.0 g, 128 mmol, 1.0 eq.) was dissolved in $CHCl_3$ (100 mL) and stirred at 0° C. To the stirred mixture was added dropwise $SOCl_2$ (18.2 g, 154 mmol, 1.2 eq.). The mixture was heated at reflux overnight, spun off the solvent on the rotary evaporator and concentrated to obtain the black mixture. The residual material was purified to 3-chloro-1,1-dideuterium-1-propylamine hydrochloride (10.8 g, 64.4%) as a white solid.

The above obtained white solid material (10.0 g, 76.3 mmol, 1.0 eq.) was dissolved in water (50 mL), followed by addition of $Na_2SO_3$ (9.61 g, 76.3 mmol, 1.0 eq.). The mixture was heated at reflux overnight and evaporated to dryness under reduced pressure, followed by addition of concentrated HCl. The insoluble material (NaCl) was removed by filtration, and the filtrate was carefully evaporated to dryness. The resultant was purified by recrystallization using $H_2O$ and EtOH. The solid was collected by filtration, and then dried to give the title compound (1) as a white solid (9.5 g, 88.3%). $^1$H NMR (500 MHz, $D_2O$): δ ppm 2.15 (t, J=7.5 Hz, 2H), 3.07 (t, J=7.5 Hz, 2H); $^{13}$C NMR (125 MHz, $D_2O$): δ ppm 22.21, 37.74 (m, $CD_2$), 47.87; m/z (ES−) 140.0 (M−H).

To a solution of compound 1 in water (10 mL) was added NaOH (1.0 eq.), and the mixture was stirred for 10 min at r.t. The mixture was evaporated under reduced pressure to dryness, giving compound 1s, which was used for further reaction without purification.

Example 2. Synthesis of 3-((L-alanyl)amino)-3,3-dideuterium-1-propanesulfonic Acid (2)

Compound is (0.30 g, 1.80 mmol, 1.0 eq.) and N-Boc-L-alanine (0.37 g, 2.0 mmol, 1.1 eq.) were mixed in dry DMF (10 mL) and cooled to 0° C., followed by addition of DCC (0.56 g, 2.7 mmol, 1.5 eq.) and HOBt (0.24 g, 1.80 mmol, 1.0 eq.) at 0° C. The mixture was stirred overnight at r.t., followed by addition of water (2 mL), and stirred for an additional hour. The insoluble material was removed by filtration, and the organic phase of the filtrate was evaporated to dryness. The residual material was dissolved in 20 mL water and washed with ethyl acetate (2×20 mL). The aqueous layer was evaporated to dryness. The residue was purified by column chromatography on silica gel using 10-30% MeOH—$CH_2Cl_2$ as eluent to afford sodium 3-((N-Boc-L-alanyl)amino)-3,3-dideuterium-1-propanesulfonic acid (0.50 g, 81.3%) as a white solid. This white solid (0.50 g, 1.5 mmol, 1.0 eq.) was added to 1N HCl (10 mL); and the mixture was stirred at 50° C. for 2 h and evaporated to dryness. The salt was removed by using ion-exchange resin (as described in General Method B above). The crude material was purified by recrystallization (MeOH and ethyl acetate). The solid product was collected by filtration, and dried under reduced pressure, giving title compound (2) (277 mg, 87.3%) as a white solid. $^1$H NMR (500 MHz, $D_2O$): δ ppm 1.49 (d, J=7.0 Hz, 3H), 1.92 (t, J=8.0 Hz, 2H), 2.90 (t, J=8.0 Hz, 2H), 3.97-4.07 (m, 1H), 8.34 (s, 1H); $^{13}$C NMR (125 MHz, $D_2O$): δ ppm 16.47, 23.71, 48.30, 49.10, 170.69; m/z (ES−) 210.8 (M−H).

Example 3. Synthesis of 3-(L-serylamino)-3,3,-dideuterium-1-propanesulfonic Acid (3)

Compound is (806 mg, 5.0 mmol, 1.0 eq.) and N-Boc-L-serine (1.03 g, 5.0 mmol, 1.0 eq) were mixed in DMF (5 mL), followed by addition of diphenylphosphoryl azide (DPPA) (1.51 g, 5.0 mmol, 1.0 eq) and $Et_3N$ (0.77 mL). The mixture was stirred at r.t. overnight and concentrated under reduced pressure. The residue was purified by flash column chromatography (MeOH/DCM, 1:4), giving sodium 3-((N-Boc-L-seryl)amino)-3,3,-dideuterium-1-propanesulfonic acid (800 mg, 58.0%) as a white solid. The solid material (250 mg, 0.71 mmol, 1.0 eq.) was added into 1N HCl aqueous solution (10 mL), and the mixture was stirred at r.t. for 1 h, concentrated under reduced pressure. The salt was removed by using ion-exchange resin (as described in General Method B above). The product was dried under vacuum, affording the title compound (3) (150 mg, 92.6%) as a white solid. $^1$H NMR (500 MHz, $D_2O$) δ ppm 1.84-1.94 (m, 2H), 2.78-2.94 (m, 2H), 3.83-3.98 (m, 2H), 4.08-4.14 (m, 1H); $^{13}$C NMR (125 MHz, $D_2O$) δ ppm 23.70, 37.80, 48.30, 54.57, 60.16, 167.59; m/z (ES+) 228.9 (M+H).

Example 4. Synthesis of 3-((L-valyl)amino)-3,3-dideuterium-1-propanesulfonic Acid (4)

Compound is (1.63 g, 10.0 mmol, 1.0 eq; prepared from compound 1 and sodium hydroxide) and N-Boc-L-valine (2.60 g, 12.0 mmol, 1.2 eq.) were dissolved in dry DMF (20 mL), followed by, at 0° C., addition of N,N'-dicyclohexylcarbodiimide (DCC, 2.47 g, 12.0 mmol, 1.2 eq.) and hydroxybenzotriazole (HOBt, 1.35 g, 10.0 mmol, 1.0 eq.). The mixture was stirred overnight at r.t., followed by addition of water (2 mL), and stirred for one more hour. The insoluble material was removed by filtration. The organic phase of the filtrate was evaporated to dryness. The residual material was dissolved in water (20 mL) and washed with ethyl acetate (2×20 mL). The aqueous phase was evaporated to dryness and the residue was purified by column chromatography on silica gel using 10-30% MeOH—$CH_2Cl_2$ as eluent, providing sodium 3-((N-Boc-L-valyl)amino)-3,3-dideuterium-1-propanesulfonic acid as a white solid (3.2 g, 88.3%).

The above obtained Boc-protected compound (3.2 g, 8.83 mmol, 1.0 eq.) was stirred in 1N HCl (30 mL) at 50° C. for 2 h. The mixture was evaporated to dryness and the crude material. The salt was removed using ion-exchange resin (General Method B) and the crude was purified by recrystallization using MeOH and ethyl acetate. The crystalline solid was collected by filtration, dried under reduced pressure, giving the title compound (4) (1.87 g, 88.1%) as a white solid. $^1$H NMR (500 MHz, $D_2O$): δ ppm 0.92-1.06 (m, 6H) 1.98 (t, J=7.5 Hz, 2H), 2.17-2.21 (m, 1H), 2.95 (t, J=8.0 Hz, 2H), 3.76 (d, J=6.5 Hz, 1H); $^{13}$C NMR (125 MHz, D20): δ ppm 17.01, 17.57, 23.73, 29.80, 48.40, 58.78, 169.18; m/z (ES−) 239.1 (M−H).

Example 5. Synthesis of 3-((L-phenylalanyl)amino)-3,3-dideuterium-1-propanesulfonic Acid (5)

Compound is (815 mg, 5.0 mmol, 1.0 eq.) and N-Boc-L-phenylalanine (1.59 g, 6.0 mmol, 1.2 eq.) were mixed in dry DMF (20 mL). The mixture was cooled to 0° C., followed by addition of DCC (1.24 g, 6.0 mmol, 1.2 eq.) and HOBt (675 mg, 5.0 mmol, 1.0 eq.) at 0° C. The reaction mixture was stirred at r.t. overnight, followed by addition of water (2 mL), and then stirred for 1 h. The solid material was removed by filtration, and the organic phase of the filtrate was evaporated to dryness. The residual material was dissolved in water (20 mL), and the aqueous solution was washed with ethyl acetate (2×20 mL). The aqueous phase was separated and evaporated to dryness. The residual material was purified by column chromatography on silica gel (eluent: methanol in $CH_2Cl_2$, from 10 to 30%), affording sodium 3-((N-Boc-L-phenylalanyl)amino)-3,3-dideuterium-1-propanesulfonic acid (1.80 g, 87.7%) as a white solid. This white solid (1.80 g, 4.39 mmol, 1.0 eq.) was treated with 1M HBr (20 mL) at 50° C. for 2 h, then the solvent was evaporated to dryness. The residual material was purified by recrystallization (EtOH and ethyl acetate). The solid was collected by filtration, and dried under reduced pressure, giving the title compound, 5, (1.07 g, 84.5%) as a white solid. $^1$H NMR (500 MHz, $D_2O$): δ ppm 1.67-1.80 (m, 2H), 2.54-2.68 (m, 2H), 3.05-3.28 (m, 2H), 4.14 (t, J=6.5 Hz, 1H), 7.28 (d, J=9.0 Hz, 2H), 7.34-7.47 (m, 3H); $^{13}$C NMR (125 MHz, $D_2O$): δ ppm 23.44, 36.87, 37.5 (m, $CD_2$), 48.18, 54.64, 128.04, 129.17, 129.27, 133.86, 168.81; m/z (ES−) 287.0 (M−H).

Example 6. Synthesis of 3-((L-histidyl)amino)-3,3-dideuterium-1-propanesulfonic Acid hydrochloride (6)

Compound is (0.93 g, 5.74 mmol, 1.0 eq.) and N-Boc-L-histidine (1.47 g, 5.74 mmol, 1.0 eq.) were mixed in DMF (10 mL), followed by addition of DPPA (1.74 g, 1.1 eq.) and $Et_3N$ (0.88 mL, 1.1 eq.). The mixture was stirred at r.t. overnight. After removal of solvent under reduced pressure, the residual material was purified by flash column chromatography (MeOH/DCM, 1:3), affording sodium 3-((N-Boc-L-histidyl)amino)-3,3-dideuterium-1-propanesulfonic acid (1.4 g, 61%) as a white solid. The solid was added into 1N HBr aqueous solution (20 mL). The mixture was stirred at r.t. for 1 h, concentrated under reduced pressure. The residual material was purified by EtOH (30 ml), The mixture was stirred at r.t. for 1 h and filtered to obtain solid. The solid was dissolved in water (5 ml) and then EtOH (30 ml) was added dropwise. After stirring at room temperature for 1 hour, the solid was collected by filtration, and dried under reduced pressure, giving the compound (6) (1.25 g, 99.0%) as a white solid. $^1$H NMR (500 MHz, $D_2O$) δ ppm 1.82 (d, J=6.8 Hz, 2H), 2.78 (t, J=7.0 Hz, 2H), 3.37 (s, 2H), 4.21 (d, J=6.0 Hz, 1H), 7.44 (s, 1H), 8.71 (s, 1H); $^{13}$C NMR (125 MHz, $D_2O$) δ ppm 23.55, 25.99, 48.21, 52.30, 118.30, 125.91, 134.32, 167.69; m/z (ES+) 278.9 (M+H).

Example 7. Synthesis of 3-($^{15}$N-amino)-1-propanesulfonic Acid (7)

To a solution of 1,3-propanesultone (0.61 g, 5.0 mmol, 1.0 eq.) in MeOH (10 mL) in a sealed tube was added $^{15}$N-labeled ammonium sulfate ($^{15}$N-enrichment, 97%, 1.0 g, 7.5 mmol, 1.5 eq.) and NaOH (0.5 g, 12.5 mmol, 2.5 eq.). The mixture was stirred overnight at 70° C., followed by addition of $NaHCO_3$ (0.63 g, 7.5 mmol, 1.5 eq.) and di-(tert-butyl) dicarbonate (1.64 g, 7.5 mmol, 1.5 eq.). After heating at reflux for 3 h, the reaction mixture was evaporated to dryness. The residual material was treated with MeOH and the insoluble material was removed by filtration. The filtrate was evaporated to dryness, and the residual material was purified by flash column chromatography on silica gel (eluent: 30% MeOH-DCM) to afford a waxy solid. This material was treated with 1N HBr (20 mL) and the mixture was stirred at 50° C. for 2 h. The mixture was evaporated to dryness and the residual material was purified by recrystallization (EtOH and $H_2O$). The solid was collected by filtration, and dried under reduced pressure, giving 3-($^{15}$N-amino)-1-propanesulfonic acid (7) (398 mg, 56.8%) as a white solid. $^1$H NMR (500 MHz, $D_2O$): δ ppm 2.06-2.16 (m, 2H), 3.01 (t, J=7.5 Hz, 2H), 3.15 (t, J=7.5 Hz, 2H); $^{13}$C NMR (125 MHz, $D_2O$): δ ppm 22.23, 38.17 (d, J=5.0 Hz), 47.82; m/z (ES+) 140.8 (M+H).

Example 8. Synthesis of 3-(L-valyl-($^{15}$N-amino))-1-propanesulfonic Acid (10)

To a solution of 1,3-propanesultone (1.22 g, 10.0 mmol, 1.0 eq.) in 20 mL MeOH/$H_2O$ (1:1) in a sealed tube was added $^{15}$N-labeled ammonium sulfate ($^{15}$N-enrichment, 98%, 2.0 g, 15.0 mmol, 1.5 eq.) and NaOH (1.0 g, 25 mmol, 2.5 eq.). The mixture was stirred overnight at 70° C., followed by addition of triethylamine (1.51 g, 15.0 mmol, 1.5 eq.) and di-tert-butyl dicarbonate (3.27 g, 15.0 mmol, 1.5 eq.). After heating at reflux for 3 h, the reaction mixture was evaporated to dryness. The residual material was treated with MeOH and the insoluble material was removed by filtration. The filtrate was evaporated to dryness and the residual material was purified by flash column chromatography on silica gel (eluent: 30% MeOH-DCM) to afford a waxy solid. This material was treated with 1N HCl (30 mL) and the mixture was stirred at 50° C. for 2 h. The mixture was evaporated to dryness and the residual material, 3-($^{15}$N-amino)-1-propanesulfonic acid (7), was used in the next step without further purification.

To a solution of compound 7 in 10 mL H₂O was added NaOH (0.4 g, 10.0 mmol, 1.0 eq.), and the mixture was stirred for 10 min at r.t. The mixture was evaporated to dryness to give sodium salt of 7, which was used in the next step without further purification.

The sodium salt of compound 7 (obtained above) and N-Boc-L-valine (3.26 g, 15.0 mmol, 1.5 eq.) were mixed in dry DMF (30 mL), cooled to 0° C., followed by addition of DCC (3.09 g, 15.0 mmol, 1.5 eq.) and HOBt (1.35 g, 10.0 mmol, 1.0 eq.). The reaction mixture was stirred overnight at r.t., followed by addition of water (2 mL), and stirred for 1 h. The insoluble material was removed by filtration, and the organic layer of the filtrate was evaporated to dryness. The residual material was dissolved in 20 mL water and the aqueous solution was washed with ethyl acetate (2×20 mL). The aqueous phase was evaporated to dryness; and the residual material was purified by column chromatography on silica gel (eluent: 10 to 30% MeOH/CH₂Cl₂), giving a waxy solid, which was treated with 1N HCl (30 mL) and stirred at 50° C. for 2 h. The mixture was evaporated to dryness and the salt was removed by using ion-exchange resin (General Method B). The residual material was purified by recrystallization (EtOH and H₂O). The solid was collected by filtration and dried under reduced pressure, giving the title compound (10) (1.23 g, 51.4%) as a white solid. $^1$H NMR (500 MHz, D₂O): δ ppm 0.99-1.08 (m, 6H), 1.91-2.03 (m, 2H), 2.12-2.25 (m, 1H), 2.93 (t, J=9.0 Hz, 2H), 3.32-3.45 (m, 2H), 3.74 (d, J=6.0 Hz, 1H); $^{13}$C NMR (125 MHz, D₂O): δ ppm 16.97, 17.54, 23.88, 29.77, 38.03 (d, J=8.8 Hz), 48.39, 58.74 (d, J=8.8 Hz), 169.13 (d, J=17.5 Hz); m/z (ES-) 237.9 (M-H).

Example 9. Synthesis of 3-((18O-L-alanyl)amino)-1-propanesulfonic Acid (13)

L-Alanine (0.91 g, 10.2 mmol, 1 eq.) was added to a solution of 4M HCl in dioxane (5.2 mL, 20.8 mmol, 2 eq.), followed by addition of H₂$^{18}$O (1.8 mL; $^{18}$O-enrichment, 98%). The mixture was stirred in a sealed tube at 100° C. for 24 h, cooled to r.t., and evaporated to dryness. The residual material was taken into a solution of 4M HCl in Dioxane (2.6 mL, 10.2 mmol, 1 eq.), followed by addition of H₂$^{18}$O (1.6 mL, $^{18}$O-enrichment, 98%). The mixture was stirred in a sealed tube at 100° C. for 24 h, cooled to r.t., and evaporated to dryness under reduced pressure, affording L-alanine-$^{18}$O₂·HCl (1.32 g, 100%; $^{18}$O-enrichment, 92%) as a white solid. To the solution of L-alanine-$^{18}$O₂·HCl (1.32 g, 10.2 mmol, 1 eq.) in MeOH (50 mL) was added N,N-diisopropylethylamine (DIPEA) (4.07 mL, 22.5 mmol, 2.2 eq.), followed by addition of Boc₂O (2.55 g, 11.22 mmol, 1.1 eq.). The mixture was stirred at 50° C. for 1 h (the mixture became clear at this point), cooled to r.t., and concentrated to dryness under reduced pressure, affording N-Boc-L-alanine-18O2 DIPEA salt as a white solid, which was used in the next step without further purification. The DIPEA salt (1 eq., obtained from the above step) was added to a solution of p-nitrophenol (1.59 g, 11.22 mmol, 1.1 eq.) in DMF (40 mL), followed by addition of DCC (3.21 g, 15.3 mmol, 1.5 eq.). The mixture was stirred at r.t. overnight. The reaction mixture was filtered, and the filtrate was concentrated under reduced pressure. The residue was purified by flash column chromatography (ethyl acetate/pet-ether, 1:10) to afford the corresponding p-nitrophenyl ester as a white solid. The solid thus obtained was dissolved in DMF (30 mL), followed by addition of sodium 3-amino-1-propanesulfonate (1.72 g, 10.2 mmol, 1.0 eq.). The mixture was stirred at 35° C. overnight, and then concentrated under reduced pressure. The residue was purified by flash column chromatography (eluent: MeOH/DCM, 1:8), affording sodium 3-((N-Boc-L-$^{18}$O-alanyl)amino)-1-propanesulfonic acid (1.5 g, 4.49 mmol; overall yield for the above steps, 44%) as a white solid. Sodium 3-((N-Boc-L-$^{18}$O-alanyl)amino)-1-propanesulfonic acid (1.5 g, 4.49 mmol) was dissolved in 1N HCl aqueous solution (20 mL). The mixture was stirred at r.t. for 1 h and evaporated to dryness. The salt was removed by using ion-exchange resin (General Method B). The product was dried under vacuum, affording the title compound (13) (0.78 g, 82.0%) as a white solid. $^{18}$O-enrichment, 92%; $^1$H NMR (D₂O, 500 MHz) δ ppm 1.46-1.51 (m, 2H), 1.88-1.97 (m, 2H), 2.86-2.92 (m, 2H), 3.30-3.37 (m, 2H), 4.20 (q, 1H, J=5 Hz); $^{13}$C NMR (D₂O, 125 MHz) δ ppm 16.45, 23.88, 38.05, 48.33, 49.08, 170.62; m/z (ES-) 211.0 (M-H).

Example 10. Synthesis of 3-(($^{18}$O-L-valyl)amino)-1-propanesulfonic Acid (15)

To a solution of L-Valine (1.2 g, 10.2 mmol) in $^{18}$O-water (1.5 g, 75.0 mmol, $^{18}$O-enrichment, 98%) was added slowly 4N HCl in 1,4-dioxane (5.1 mL, 20.4 mmol). The mixture was sealed with stopper, heated at 100° C. for 24 h, and then cooled to r.t., and evaporated (up to 60° C. bath temperature) to dryness. The above process was repeated once, giving $^{18}$O-L-Valine hydrochloride as a yellow solid (1.57 g, 100%, $^{18}$O-enrichment, 91.4%), which was used for the next step directly.

To a solution of $^{18}$O-L-Valine hydrochloride (1.57 g, 10.2 mmol, 1.0 eq.) in dichloromethane (30 mL), was added P-nitrophenol (1.5 g, 10.7 mmol) and DCC (2.3, 11.2 mmol), then cooled under zero degrees. The mixture was stirred for 2 hours under r.t. TLC analysis (DCM:MeOH=10:1) showed no starting material remaining. The insoluble material was removed by filtration and washed with DCM (30 mL). The combined filtrate was concentrated, and purified by silica gel chromatography (EtOAc:hexane, 4:1), giving a yellow liquid (2.8 g, 80.2%). This liquid (2.2 g, 6.4 mmol, 1.0 eq.) and sodium 3-amino-1-propanesulfonate (1.0 g, 6.4 mmol, 1.0 eq.) were mixed in DMF (22 mL). The mixture was stirred at 35° C. for 24 h. The solvent was removed under reduced pressure, and the residue was purified by silica gel chromatography (DCM:MeOH, 4:1), giving sodium 3-((N-Boc-($^{18}$O-L-valyl))amino)-1-propanesulfonic acid as a white solid (1.5 g, 65.0%). $^1$H NMR (500 MHz, D₂O) δ ppm 0.95 (s, 6H), 1.43 (s, 9H), 1.95 (s, 2H), 2.04 (s, 1H), 2.91 (s, 2H), 3.37 (s, 2H), 3.77 (s, 1H).

The solution of the above obtained solid (1.5 g, 4.1 mmol) in 1N HCl (20 mL) was stirred at 60° C. for 1 h. The solvent was removed under reduced pressure. The salt was removed by using ion-exchange resin (General Method B). The product was dried under vacuum, affording the title compound, 15 (686 mg, 70.0%) as a white solid. $^{18}$O-Enrichment, 94% (by ES-MS); $^1$HNMR (500 MHz, D20) δ ppm 0.98-1.10 (m, 6H), 1.97 (s, 2H), 2.20 (d, J=4.8 Hz, 1H), 2.93 (s, 2H), 3.38 (d, J=4.5 Hz, 2H), 3.75 (s, 1H); $^{13}$C NMR (126 MHz, D20) δ ppm 17.05, 17.61, 23.94, 29.82, 38.13, 48.47, 58.78, 169.15; m/z (ES-) 238.9 (M-H).

Example 11. Synthesis of 3-(($^{18}$O-L-phenylalanyl)amino)-1-propanesulfonic Acid (16)

To a mixture of L-phenylalanine (1.0 g, 6.05 mmol, 1.0 eq.) and $^{18}$O-water (1.3 mL, $^{18}$O-enrichment, 98%) was added a saturated hydrochloride (HCl) solution in 1,4-dioxane (3.0 mL, 12.0 mmol, 2.0 eq.). The mixture was stirred at 100° C. for 24 h, then cooled to r.t., and evaporated to dryness under reduced pressure. To the residual material was added $^{18}$O-water (1.5 mL, $^{18}$O-enrichment, 98%), followed by addition of HCl solution in 1,4-dioxane (1.6 mL). The mixture was stirred at 100° C. for 24 h, then cooled to r.t., and evaporated to dryness under reduced pressure, giving $^{18}$O-L-phenylalanine as a white solid (1.0 g, 100%; $^{18}$O-enrichment, 96%).

To $^{18}$O-L-phenylalanine (1.0 g, 6.1 mmol, 1.0 eq.) in methanol (20 mL) was added (Boc)$_2$O (1.45 g, 6.65 mmol, 1.1 eq.) and triethylamine (1.8 g, 18.0 mmol, 3.0 eq.). The mixture was stirred at 30° C. for 2 h, then evaporated to dryness under reduced pressure. The residue was dissolved in dichloromethane (10 mL), followed by addition of dicycylohexylcarbodiimide (1.24 g, 6.1 mmol, 1.0 eq.) and N-hydroxysuccinimide (0.60 g, 6.2 mmol, 1.05 eq.). The mixture was stirred at r.t. overnight. The insoluble material was removed by filtration, and the filtrate was evaporated under reduced pressure. The residual material was purified by flash column chromatography on silica gel (eluent: CH$_2$Cl$_2$/methanol, 10:1), giving a white solid (1.4 g). This white solid was dissolved in DMF (20 mL), followed by addition of sodium 3-aminopropane-1-sulfonate (610 mg, 3.84 mmol). The mixture was stirred at r.t. for 2 h, and solvent was removed in vacuo. The residual material was purified by flash column chromatography on silica gel (eluent: CH$_2$Cl$_2$/methanol, from 10:1 to 5:1), giving sodium 3-((N-Boc-($^{18}$O-L-phenylalanyl))amino)-1-propanesulfonic acid as a white solid (1.3 g, 82.0%). The obtained compound was dissolved in 1N HCl (20 mL). The mixture was stirred for 4 h, and then concentrated in vacuo. The salt was removed by using ion-exchange resin (General Method B). To the residual material was added ethanol (20 mL), and the mixture was stirred at r.t. for 5 min. The solid was collected by filtration, washed with ethanol (5 mL), and dried under reduced pressure, affording the title compound (400 mg, 40.0%) as a white solid. $^{18}$O-enrichment, 87%; $^1$H NMR (500 MHz, D$_2$O) δ ppm 1.68-1.69 (m, 2H), 3.02-3.10 (m, 2H), 2.53-2.56 (m, 2H), 3.14-3.24 (m, 2H), 4.06 (t, J=8.0 Hz, 0.1H), 7.21 (d, J=7.0 Hz, 2H), 7.32-7.37 (m, 3H), 8.09 (s, 1H); $^{13}$C NMR (125 MHz, D$_2$O) δ ppm 23.6, 36.8, 38.0, 48.1, 54.6, 128.0, 129.1, 129.2, 133.8, 168.7; m/z (ES+) 288.9 (M+H), 310.9 (M+Na).

Example 12. Synthesis of 3-(($^{18}$O-L-histidyl)amino)-1-propanesulfonic Acid hydrobromide (17)

L-Histidine (1.55 g, 10 mmol, 1.0 eq.) was added to a solution of 4M HCl in Dioxane (7.5 mL, 30 mmol, 3.0 eq.), followed by addition of H$_2$$^{18}$O (2.0 g, 98% $^{18}$O-enrichment). The mixture was stirred in a sealed tube at 100° C. for 24 h. The reaction mixture was cooled to r.t. and dried under vacuum. To the residue was added 4M HCl in Dioxane (2.5 mL, 10 mmol, 1.0 eq.), followed by addition of H$_2$$^{18}$O (2.0 g, $^{18}$O-enrichment, 98%). The mixture was stirred in a sealed tube at 100° C. for 24 h. The reaction mixture was cooled to r.t., evaporated to dryness, and further dried under vacuum, to afford L-His-$^{18}$O$_2$.2HCl (2.32 g, 100%, with 93.8% of $^{18}$O-enrichment) as an off-white solid. The $^{18}$O-enriched L-histidine dihydrochloride (2.32 g, 10 mmol, 1.0 eq.) was dissolved in MeOH (50 mL), followed by addition of Et$_3$N (4.55 g, 45 mmol, 4.5 eq.) and Boc$_2$O (5.45 g, 25 mmol, 2.5 eq.) subsequently. The mixture was stirred at 50° C. for 1 h (the mixture became clear at this point) and then was cooled to r.t., and concentrated under reduced pressure, to afford the corresponding TEA salt as a light-yellow solid. This light-yellow material (1.0 eq.) was added to a solution of p-nitrophenol (1.39 g, 10 mmol, 1.0 eq.) in DCM (40 mL), followed by addition of DCC (2.27 g, 11 mmol, 1.1 eq.). The mixture was stirred at r.t. overnight. The insoluble material was removed by filtration, and the filtrate was concentrated under reduced pressure. The residual material was purified by flash column chromatography (eluent: DCM/EA/PE, 2:1:7) to afford the corresponding 4-nitrophenyl ester (3.0 g, 63.0%) as a white solid. The ester (3.0 g, 6.27 mmol, 1.0 eq.) was dissolved in DMF (30 mL), followed by addition of sodium 3-aminopropane-1-sulfonate (1.0 g, 6.27 mmol, 1.0 eq.). The mixture was stirred at r.t. overnight. The reaction mixture was concentrated under reduced pressure, and the residual material was purified by flash column chromatography (eluent: MeOH/DCM, 1:8) to afford sodium 3-((N,1-bisBoc-($^{18}$O-L-histidyl))amino)-1-propanesulfonic acid (2.27 g, 72.3%) as a white solid. The white solid (2.27 g, 4.7 mmol) was taken into 1N HBr aqueous solution (20 mL). The mixture was stirred at r.t. for 1 h, concentrated under reduced pressure, and dried under vacuum. The residual material was purified by recrystallization (EtOH and H$_2$O). The solid was collected by filtration, and dried under reduced pressure, affording the title compound (17) (1.5 g, 92.0%) as a white solid. $^{18}$O-enrichment, 93.7%; $^1$H NMR (D$_2$O, 500 MHz) δ ppm 1.77-1.94 (m, 2H), 2.72-2.88 (m, 2H), 3.22-3.32 (m, 1H), 3.32-3.46 (m, 3H), 4.18-4.28 (m, 1H), 7.47 (s, 1H), 8.74 (s, 1H); $^{13}$C NMR (D$_2$O, 125 MHz) δ ppm 23.75, 25.98, 38.17, 48.26, 52.33, 118.30, 125.95, 134.34, 167.68; m/z (ES+) 279.0 (M+H).

Example 13. Synthesis of 3-((1-13C-L-valyl)amino)-1-propanesulfonic Acid (25)

Sodium 3-amino-1-propanesulfonic acid (1.10 g, 6.8 mmol, 1.5 eq.) and N-Boc-L-valine-1-$^{13}$C (1.0 g, 4.61 mmol, 1.0 eq.) were dissolved in dry DMF (10 mL), followed by, at 0° C., addition of N,N'-dicyclohexylcarbodiimide (DCC, 1.4 g, 6.8 mmol, 1.5 eq.) and hydroxybenzotriazole (HOBt, 0.62 g, 4.61 mmol, 1.0 eq.). The mixture was stirred overnight at r.t., followed by addition of water (2 mL), and stirred for one more hour. The insoluble material was removed by filtration. The organic phase of the filtrate was evaporated to dryness. The residual material was dissolved in water (20 mL) and washed with ethyl acetate (2×20 mL). The aqueous phase was evaporated to dryness and the residue was purified by column chromatography on silica gel (eluent, MeOH—CH$_2$Cl$_2$, 10-30%), providing sodium 3-((N-Boc-1-$^{13}$C-L-valyl)amino)-1-propanesulfonic acid as a white solid (1.2 g, 72.0%).

The above obtained Boc-protected compound (1.2 g, 3.3 mmol, 1.0 eq.) was stirred in 1N HCl aqueous solution (30 mL) at 50° C. for 2 h. The mixture was evaporated to dryness. The salt was removed using ion-exchange resin (General Method B). The residual material was purified by recrystallization (EtOH and H$_2$O). The solid was collected by filtration and dried under reduced pressure, giving the title compound (25) (0.65 g, 75.4%) as a white solid. $^1$H NMR (500 MHz, D$_2$O): δ ppm 0.97-1.05 (m, 6H), 1.90-2.00 (m, 2H), 2.21-2.23 (m, 1H), 2.91 (t, J=7.5 Hz, 2H), 3.29-3.43 (m, 2H), 3.69-3.75 (m, 1H), 8.49 (s, 1H); $^{13}$C NMR (125 MHz, D$_2$O): δ ppm 16.97, 17.54, 23.87, 29.77, 38.04, 48.39, 58.50, 58.92, 169.14, 169.23; m/z (ES−) 238.0 (M−H).

Example 14. Synthesis of 3-(($^{18}$O-L-valyl)amino)-3,3-dideuterium-1-propanesulfonic Acid (29)

Compound is (250 mg, 1.53 mmol, 1.0 eq.) and N-Boc-L-(1,1-di-$^{18}$O)-valine 4-notrophenyl ester (624 mg, 1.84 mmol, 1.2 eq.) were mixed in dry DMF (20 mL). The mixture was stirred overnight at r.t., followed by evaporation under reduced pressure to dryness. The residual material was purified by column chromatography on silica gel (eluent: MeOH in $CH_2Cl_2$, 10 to 30%), affording sodium 3-((N-Boc-$^{18}$O-L-valyl)amino)-3,3-dideuterium-1-propanesulfonic acid (400 mg, 71.7%) as a white solid. This solid material was mixed with 1N HCl (30 mL); and the mixture was stirred at 50° C. for 2 h. The mixture was evaporated to dryness. The salt was removed by using ion-exchange resin (General Method B). The residual material was purified by recrystallization (EtOH and $H_2O$). The solid was collected by filtration and dried under reduced pressure, giving the title compound 29 (283 mg, 89.8%) as a white solid. $^1$H NMR (500 MHz, D2O): δ ppm 1.00-1.08 (m, 6H), 1.97 (t, J=7.5 Hz, 2H), 2.16-2.26 (m, 1H), 2.94 (t, J=8.0 Hz, 2H), 3.75 (d, J=6.0 Hz, 1H), 8.48 (s, 1H); $^{13}$C NMR (125 MHz, D2O): δ ppm 17.03, 17.59, 23.75, 29.81, 37.59 (m, CD2), 48.42, 58.79, 169.16; m/z (ES−) 240.9 (M−H).

Example 15. Synthesis of 3-((L-cysteinyl)amino-)-3,3-dideuterium-1-propanesulfonic Acid (33)

Compound is (0.7 g, 4.3 mmol, 1.0 eq.) and N-Boc-L-cysteine (1.4 g, 4.3 mmol, 1.0 eq.) were dissolved in dry DMF (15 mL), followed by, at 0° C., addition of DCC (1.4 g, 6.5 mmol, 1.5 eq.) and HOBt (0.6 g, 4.6 mmol, 1.1 eq.). The mixture was stirred overnight at r.t., followed by addition of water (2 mL), and stirred for one more hour. The insoluble material was removed by filtration. The organic phase of the filtrate was evaporated to dryness. The residual material was dissolved in water (20 mL) and washed with ethyl acetate (2×20 mL). The aqueous phase was evaporated to dryness and the residue was purified by column chromatography on silica gel (eluent: MeOH—$CH_2Cl_2$, 10-30%), providing sodium N-Boc-3-((L-cysteinyl)amino-)-3,3-dideuterium-1-propanesulfonic acid as a white solid (1.2 g, 59.8%). The above obtained Boc-protected compound (1.2 g, 2.57 mmol, 1.0 eq.) was stirred in 1N HCl (30 mL) at 50° C. for 2 h. The mixture was evaporated to dryness. The salt was removed by using ion-exchange resin (General Method B). The residual material was purified by recrystallization (EtOH and $H_2O$). The crystalline solid was collected by filtration and dried under reduced pressure, giving the title compound (33) (0.57 g, 83.3%) as a white solid. $^1$H NMR (500 MHz, $D_2O$): δ ppm 1.97 (t, J=7.5 Hz, 2H), 2.95 (t, J=6.0 Hz, 2H), 3.01-3.13 (m, 2H), 4.16 (t, J=6.0 Hz, 1H); $^{13}$C NMR (125 MHz, $D_2O$): δ ppm 23.70, 24.73, 48.34, 54.55, 167.83; m/z (ES+) 244.9 (M+H).

Example 16. General Method for Pharmacokinetic Study of Compounds of the Invention Forty-two male ICR mice, body-weight of 19 to 21 g, are randomized into 7 groups. The animals are administered with an aqueous solution of a test compound by oral gavage. Blood samples are collected into tubes pre-loaded with heparin anticoagulating agent, at time 0.167, 0.5, 1, 2, 4, 8, and 12 h after administration. Blood samples are centrifuged, and plasma samples are isolated for analysis of the test compound (including compounds administered, metabolites, and/or prodrugs). A 400 µL blood sample is collected from each animal, and then the animal is put to sleep with barbiturate anesthesia; perfusion is performed (through the main vein of the heart) with saline at a rate of 5 mL/min., for 6 min. The brain is collected and kept at −40° C. until the sample is analyzed. The protein in the plasma is precipitated and the analytical sample is analyzed on an AB4000-Q-Trap UPLC-MS/MS instrument.

Figure 2:
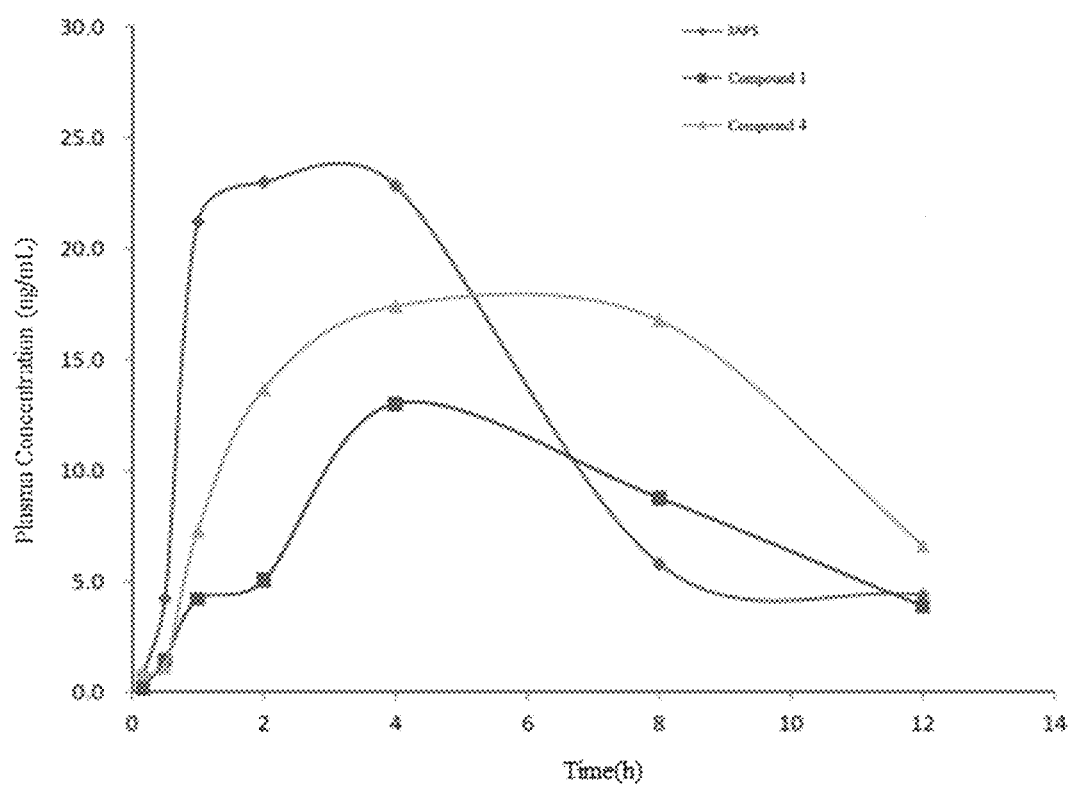
FIG. 2 shows the plasma concentration of the metabolite (M, 2-carboxy-1-ethanesulfonic acid) following an oral administration of non-isotope enriched 3APS (3APS of natural abundance), compound 1, and compound 4, respectively. Curves labeled with -♦-, -■-, and -▲- represent 3APS (of natural abundance), compound 1, and compound 4, respectively. All compounds were administered at a molar-equivalent dose (0.72 mmol/kg). (Reproduced from U.S. Pat. No. 10,472,323 with permission.)

The results of an exemplary pharmacokinetic study are presented in FIGS. 1 and 2. FIG. 1 shows plasma compound concentration-time curves following an oral administration of 3APS (of natural abundance, i.e., not isotope-enriched), compound 1 and compound 4. In the figure, curves labeled with -♦-, -■-, and -▲- represent plasma drug concentration following administration of 3APS (of natural abundance), compounds 1 and 4, respectively; and the curve labeled with -x- represents plasma prodrug concentration following administration of 4. The results indicate that at the mole-equivalent oral dose, the isotope-enriched compounds 1 and 4 improved plasma drug exposure significantly, with close to 2-fold increase of Cmax for the drug concentration following the administration of compound 4. Furthermore, compound 4 (a prodrug of compound 1) was converted easily to compound 1 in the subject (FIG. 1). In addition, the isotope-enriched compounds (1 and 4) delayed drug metabolism.

FIG. 2 shows the plasma concentration of the metabolite (M, 2-carboxy-1-ethanesulfonic acid) following an oral administration of 3APS (of natural abundance), compound 1, and compound 4, with the curves labeled with -♦-, -■-, and -▲- representing 3APS (of natural abundance), 1, and 4, respectively. At the 2-h time point, for example, plasma drug concentrations from the compounds 1 and 4 were higher than that from 3APS (of natural abundance), while the concentration of metabolite in plasma was much lower following administration of isotope-enriched compounds compared to administration of 3APS (of natural abundance).

Example 17. Efficacy Evaluation Experiment of Middle Cerebral Artery Occlusion (MCAO) Model Making the model: SD rats were anesthetized by intraperitoneal injection of 12% chloral hydrate (360 mg/kg) and fixed on the operating table. The room temperature was maintained at about 25° C. The right neck skin was cut, and the right common carotid artery, external carotid artery and their branches were separated and ligated. The right common carotid artery, internal carotid artery and external carotid artery were separated, and the extracranial branch pterygopalatine artery could be seen at the bubble. The branch was ligated at the root. The preparation line was ligated and the artery clamp placed at the distal end of the external carotid artery. After the external carotid artery was straightened, it was cut at the bifurcation, and a nylon line with a diameter of 0.26 mm was inserted for 17~20 mm, entering from the external carotid artery through the internal carotid artery to the starting end of the middle cerebral artery (MCA) to the proximal end of the anterior cerebral artery to block all blood flow sources of the MCA. After 1.5 h, the nylon suture was pulled out to recanalize the blood flow. At the time of reperfusion, the relevant test objects were given at a single time, the suture was ligated and the skin was sutured, and the operating rats were raised in separate cages. After 24 hours of ischemia, behavioral score and TTC staining were measured and performed.

Figure 3:
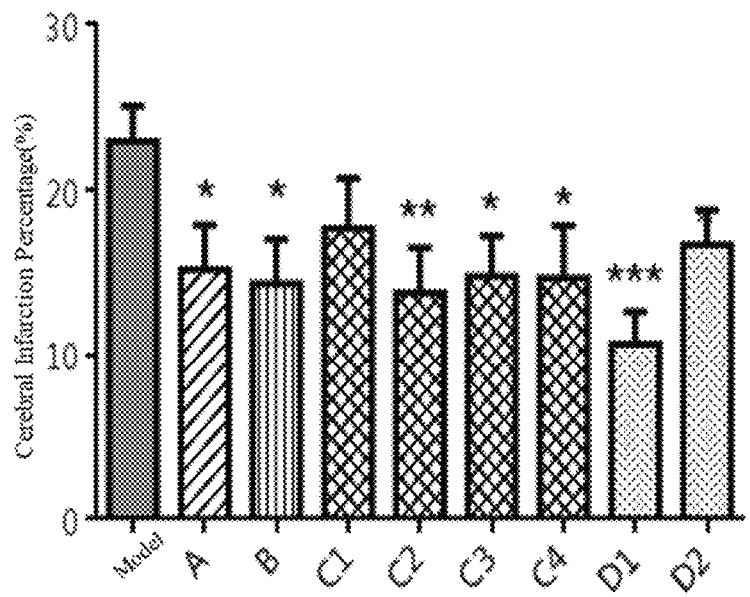
FIG. 3 shows the effect of tested compounds on the cerebral infarction area in an animal model, expressed as a percentage of the infarct area and the total area, wherein the model group contains: A: Nimodipine, 0.5 mg/kg; B: Butylphthalide, 5 mg/kg; C1: compound 1, 1 mg/kg; C2: compound 1, 2 mg/kg; C3: compound 1, 8 mg/kg; C4: compound 1, 32 mg/kg; D1: compound 4, 25 mg/kg; D2: Compound 4, 100 mg/kg.
Figure 4:
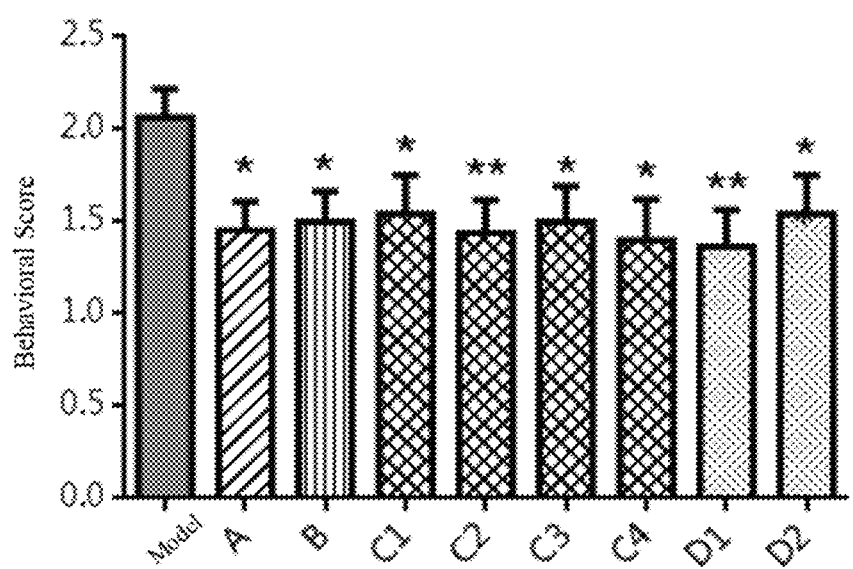
FIG. 4 shows the behavioral score of tested compounds in an animal model, wherein the model group contains: A: Nimodipine, 0.5 mg/kg; B: Butylphthalide, 5 mg/kg; C1: compound 1, 1 mg/kg; C2: compound 1, 2 mg/kg; C3: compound 1, 8 mg/kg; C4: compound 1, 32 mg/kg; D1: compound 4, 25 mg/kg; D2: Compound 4, 100 mg/kg.

Animal grouping: animals were divided into 8 groups: model=model group, A=nimodipine (0.5 mg/kg), B=butylphthalide (5 mg/kg), C1=compound 1 (1 mg/kg), C2=compound 1 (2 mg/kg), C3=compound 1 (8 mg/kg), C4=compound 1 (32 mg/kg), D1=compound 4 (25 mg/kg) and D2=compound 4 (100 mg/kg); All groups were administered intravenously. The detection indexes were the percentage of cerebral infarction and behavioral score. The behavioral scoring criteria were: no neurological dysfunction, 0; Lift the tail and bend the opposite forelimb, 1 point; 2 points for those who spin on the ground when walking and have no body deviation to the opposite side when stationary; Those who spin on the ground while walking and lean to the opposite side when stationary, 3 points; Severe disturbance of consciousness, 4 points; and Death, 5 points. The experimental results are shown in FIG. 4. After the behavioral scoring, animals were decapitated and the brain was taken. The area of cerebral infarction was measured by TTC staining: the average coronal section of the brain was cut into 5 pieces, placed in TTC solution and incubated at 37° C. for about 10-15 min. The infarct area was not stained, whereas the normal brain tissue stained red. After taking photos with a digital camera, the percentage of necrotic area in the whole brain was calculated. The experimental results are shown in FIG. 3.

Example 18. Pharmacodynamic and Pharmacological Evaluation of Dementia Model Caused by Cerebral Ischemia-Reperfusion 140 healthy C57BL/6J mice, including 70 males and 70 females, were used. 1% Pentobarbital Sodium (50 mg/kg) was injected intraperitoneally to anesthetize the mice. The back position was fixed, the neck hair was removed, and the common carotid arteries were cut along the middle of the neck after iodophor disinfection. The common carotid arteries were separated, clamped with a noninvasive artery clamp for 15 minutes, released for 10 minutes, and then clamped for 10 minutes. Penicillin powder was then applied to suture muscles and skin. The sham operation group was not clamped, and other operations were the same as for the model group. Because the operation had a certain mortality, a total of 98 mice survived, including 47 males and 51 females. Mice were divided into 6 groups: sham operation group, model group, positive control group (donepezil) and test compound group (different doses). Test compounds were administered by gavage to each group on the next day of modeling. The compound group was given compounds once a day in the morning and evening, and the volume of each gavage was 10 ml/kg. Half of the animals in the sham operation group and the model group were given the same amount of distilled water, and half of the animals were given the same amount of 1% sodium carboxymethylcellulose solution. From the 16th day of administration, Y maze, new object discrimination (days 17-20), spontaneous activity (days 20), Morris water maze (days 23-28) and dark avoidance experiment (days 29-30) were carried out successively. During the behavioral experiment, the administration of compound was continued until the animals were sacrificed.

Figure 5:
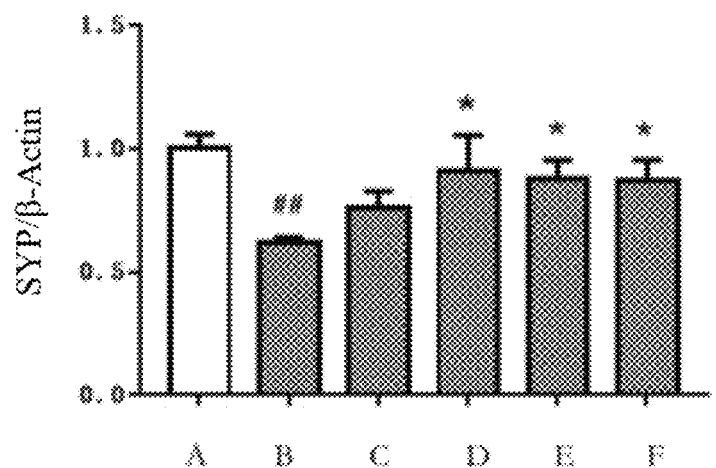
FIG. 5 shows the effect of compound 4 on the expression of SYP in hippocampus of a mouse model for dementia, induced by cerebral ischemia-reperfusion (n=15-17, mean±SEM), wherein: A. Sham operation group; B. Model group; C. Compound 4, 85 mg/kg, bid; D. Compound 4, 170 mg/kg, bid; E. Compound 4, 340 mg/kg, bid; F. Donepezil, 1.3 mg/kg. Compared with sham operation group, ## $P<0.01$; Compared with the model group, * $P<0.05$.
Figure 6:
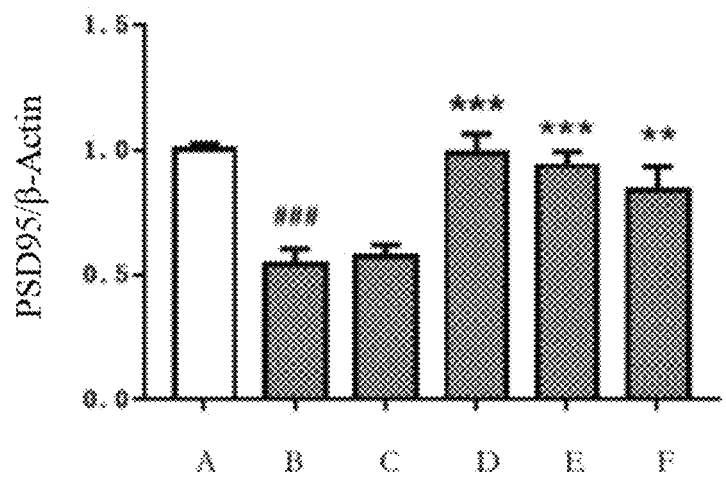
FIG. 6 shows the effect of compound 4 on the expression of PSD95 in hippocampus of a mouse model for dementia, induced by cerebral ischemia-reperfusion (n=15-17, mean±SEM): A. Sham operation group; B. Model group; C. Compound 4, 85 mg/kg, bid; D. Compound 4, 170 mg/kg, bid; E. Compound 4, 340 mg/kg, bid; F. Donepezil, 1.3 mg/kg. Compared with sham operation group: ### $P<0.001$; Compared with the model group:  $P<0.01$, * $P<0.001$.
Figure 7:
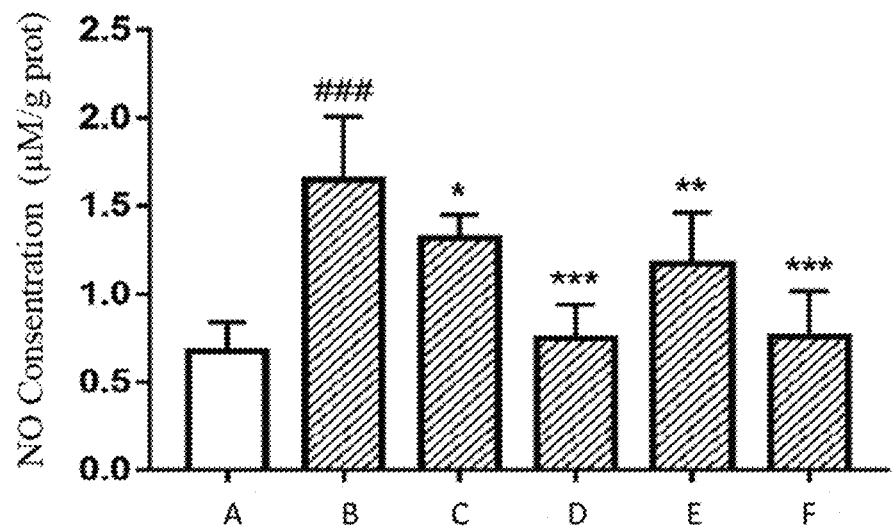
FIG. 7 shows the effect of compound 4 on NO concentration in cerebral cortex of a rat model for dementia, caused by multiple cerebral infarction (n=12-14, mean±SEM): A. Sham operation group; B. Model group; C. Compound 4, 120 mg/kg, bid; D. Compound 4, 240 mg/kg, bid; E. Compound 4, 480 mg/kg, bid; F. Donepezil, 0.9 mg/kg. Compared with sham operation group: ### $P<0.001$; Compared with the model group:  $P<0.01$, * $P<0.001$.
Figure 8:
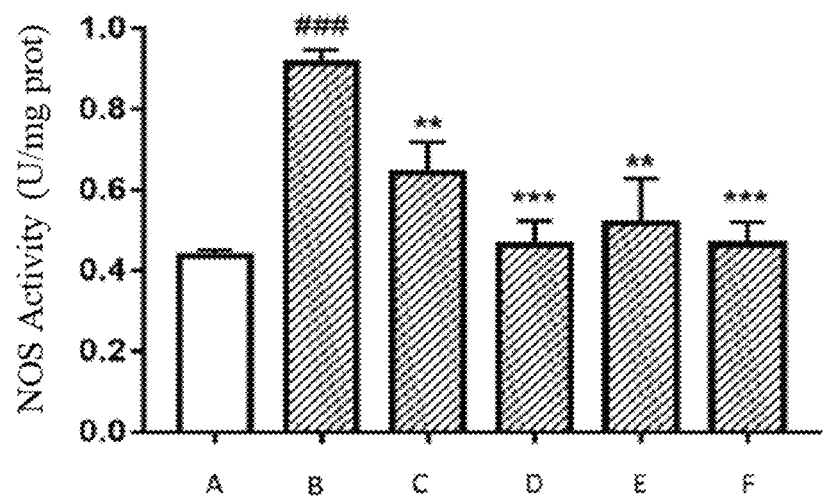
FIG. 8 shows the effect of compound 4 on NOS activity in cerebral cortex of a rat model for dementia, caused by multiple cerebral infarction (n=12-14, mean±SEM): A. Sham operation group; B. Model group; C. Compound 4, 120 mg/kg, bid; D. Compound 4, 240 mg/kg, bid; E. Compound 4, 480 mg/kg, bid; F. Donepezil, 0.9 mg/kg. Compared with sham operation group: ### $P<0.001$; Compared with the model group:  $P<0.01$, * $P<0.001$.
Figure 9:
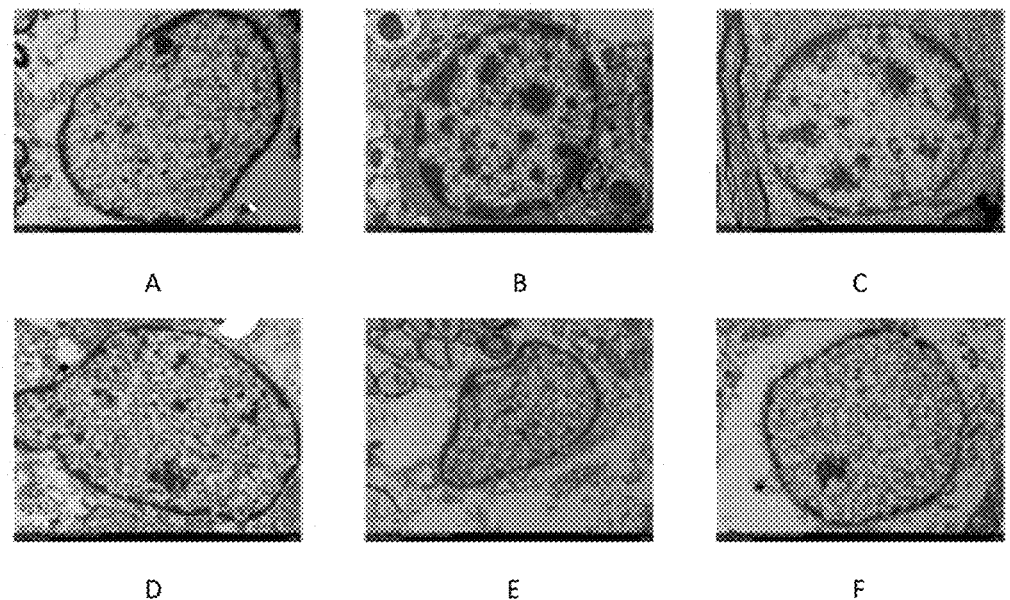
FIG. 9 shows the effect of compound 4 on the ultrastructure of neurons in cerebral cortex of a rat model for dementia, caused by multiple cerebral infarction (n=4, ×4000, 2.0 μm): A. Sham operation group; B. Model group; C. Compound 4, 120 mg/kg, bid; D. Compound 4, 240 mg/kg, bid; E. Compound 4, 480 mg/kg, bid; F. Donepezil, 0.9 mg/kg.
Figure 10:
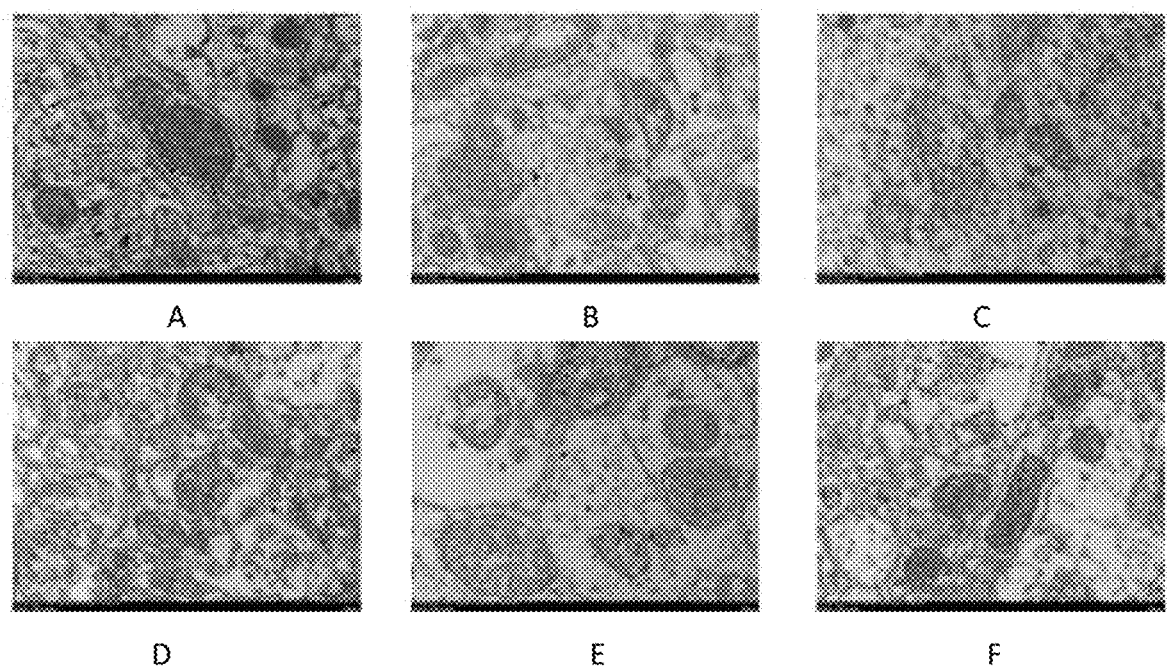
FIG. 10 shows the effect of compound 4 on the ultrastructure of neurons in cerebral cortex of a rat model for dementia, caused by multiple cerebral infarction (n=4, ×12000, 0.5 μm): A. Sham operation group; B. Model group; C. Compound 4, 120 mg/kg, bid; D. Compound 4, 240 mg/kg, bid; E. Compound 4, 480 mg/kg, bid; F. Donepezil, 0.9 mg/kg.
Figure 11:
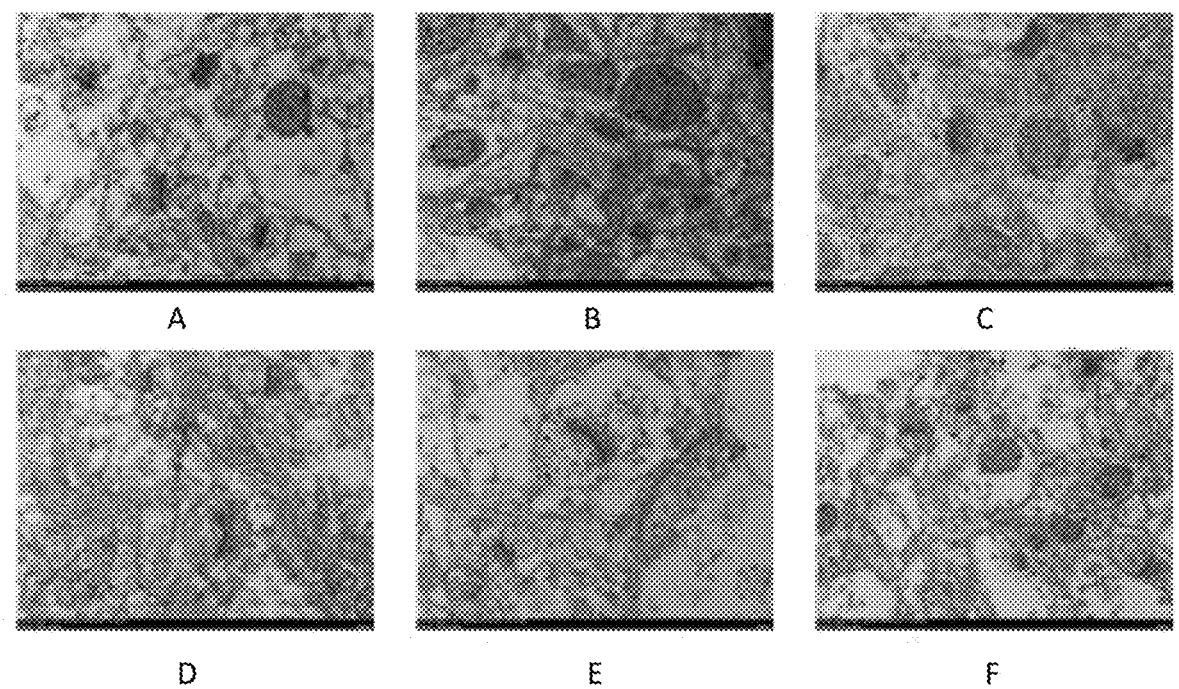
FIG. 11 shows the effect of compound 4 on synaptic ultrastructure of cerebral cortical neurons in a rat model for dementia, caused by multiple cerebral infarction (n=4, ×12000, 0.5 μm): A. Sham operation group; B. Model group; C. Compound 4, 120 mg/kg, bid; D. Compound 4, 240 mg/kg, bid; E. Compound 4, 480 mg/kg, bid; F. Donepezil, 0.9 mg/kg.

The main pathological index included: investigation of the improvement of learning and memory impairment by the compound in the pathogenic model of cerebral ischemia-reperfusion using behavioral experimental methods such as Y maze, new object discrimination, spontaneous activity, Morris water maze and passive avoidance experiment (dark avoidance); investigation of the ultrastructure of nerve cells (including nucleus, mitochondria and synapse) by HE staining and immunofluorescence; detection of expression of synaptic associated proteins SYP and PSD95 by Western blotting; and detection of expression of apoptosis-related proteins Bcl-2 and Bax by Western blotting. The experimental results for compound 4 on the expression of SYP and PSD95 in the hippocampus of dementia model mice induced by cerebral ischemia-reperfusion are shown in FIG. 5 and FIG. 6 and in Table V below. Experimental results were analyzed statistically using IBM SPSS 21.0 software. The differences between groups were compared by one-way ANOVA or two-way ANOVA (water maze directional navigation) and LSD test. Experimental data were expressed by "mean±SEM", $P<0.05$.

The results show that compound 4 significantly improved the spontaneous alternating response rate of mice in the Y maze experiment, improved the priority index and discrimination coefficient of mice to new objects in the new object discrimination experiment, prolonged the swimming time of mice in the target quadrant in the water maze test experiment, improved the percentage of swimming distance in the target quadrant, increased the number of times of crossing the platform, and prolonged the incubation period of mice entering the dark room in the dark avoidance experiment, showing that compound 4 can significantly improve the working memory, image recognition memory, spatial memory and long-term memory impairment of vascular dementia mice caused by cerebral ischemia-reperfusion.

TABLE V

Results of cognitive tests in mouse model of dementia caused by cerebral ischemia-reperfusion in Example 18 (n = 15-17).

| | Compared with model group | |
|---|---|---|
| Parameter | Sham group | Test group |
| Spontaneous alternating response rate | $p < 0.001$ | $p < 0.05$ |
| Priority index for new objects | $p < 0.001$ | $p < 0.05$ |
| Discrimination coefficient for new objects | $p < 0.001$ | $p < 0.05$ |
| Swimming time in target quadrant | $p < 0.01$ | $p < 0.05$ |
| Percentage of swimming distance | $p < 0.01$ | $p < 0.05$ |
| Times of crossing the platform | $p < 0.001$ | $p < 0.01$ |
| The incubation period for entering the darkroom | $p < 0.01$ | $p < 0.05$ |

Further, compound 4 significantly improved the arrangement and morphology of neuronal cells in hippocampal CA1 area and CA3 area of mice compared with the model group, significantly reduced the deep staining pyknosis of nuclei, significantly reduced the deep staining pyknosis of nuclei in cerebral cortex, increased the expression of MBP in hippocampal CA1 area and cerebral cortex, increased the expression of SYP and PSD95, increased the expression of Bcl-2 and reduced the expression of Bax, Results are given in Table VI below. These results show that compound 4 can have a protective effect on nerve cells, e.g. by improving the expression level of synapse related proteins and reducing cell apoptosis.

TABLE VI

Results for cellular expression levels in mouse model of dementia caused by cerebral ischemia-reperfusion in Example 18 (n = 15-17).

| | Compared with model group | |
|---|---|---|
| Parameter | Sham operation group | Test group |
| SYP expression | $p < 0.01$ | $p < 0.05$ |
| PSD95 expression | $p < 0.001$ | $p < 0.001$ |
| Bcl-2 expression | $p < 0.01$ | $p < 0.01$ |
| Bax expression | $p < 0.001$ | $p < 0.01$ |

Example 19. Pharmacodynamic Evaluation of Dementia Model Caused by Multiple Cerebral Infarction 135 SPF grade SD rats (75 females, 60 males, weighing 200-220 g) were used. Anesthesia was performed by intraperitoneal injection of 3.5% chloral hydrate (350 mg/kg). After dorsal fixation, neck hair removal and iodophor disinfection, animals were cut along the middle of the neck to separate the right common carotid artery, external carotid artery and internal carotid artery. The common carotid artery was temporarily clamped by the artery clamp, the left external carotid artery was retrogradely punctured to the beginning of the left internal carotid artery with a pediatric scalp needle, and then 0.4 ml of embolic normal saline suspension was slowly injected with a syringe (the preparation of embolic normal saline suspension was as follows: blood was collected from the abdominal aorta of the same rat, dried naturally in a 37° C. incubator, and prepared for 80-200 minutes to form a blood clot; during application, 0.3 ml normal saline was added to every 10 mg blood clot), and the common carotid artery clamp was opened at the same time, then the external carotid artery was ligated and the skin was sutured. In the sham operation group, 0.4 ml normal saline was used instead of embolic suspension. The experimental animals were randomly divided into 6 groups according to weight balance, as follows: sham operation group, model group, positive control group (donepezil) and test compound group (different doses). There were 12-14 rats in each group. The animals in each group began to give drugs by gavage after modeling until the end of the experiment. The animals underwent Y maze experiment on the 16th day of administration, new object discrimination experiment on the 17th-20th day, Morris water maze experiment on the 22nd-27th day, and dark avoidance experiment on the 28th-29th day. On the 30th day, animals were sacrificed and tissues harvested for analysis.

The main pathological indexes included investigation of the improvement of learning and memory impairment in the dementia model animal by test compound using behavioral experimental methods such as Y maze, new object discrimination, Morris water maze and passive avoidance test (dark avoidance); investigation of the protective effect of test compound on mitochondria by detecting the content of ATP in hippocampus and cortex of rats; and investigation of levels of oxidative stress in the rat brain by measuring activity of superoxide dismutase (SOD, which is an oxygen free-radical scavenger), glutathione peroxidase (GSH-Px, which scavenges lipid peroxides induced by reactive oxygen species and —OH), nitric oxide synthase (NOS), malondialdehyde (MDA), and nitric oxide (NO). The ultrastructure of nerve cells (including nucleus, mitochondria and synapse) was investigated using immunofluorescence and transmission electron microscope. Expression of synaptic associated proteins SYP and PSD95 was detected by Western blotting. Experimental results for compound 4 on the concentration of nitric oxide (NO), the activity of nitric oxide synthase (NOS) and the ultrastructure of nerve cells in the rat model of dementia caused by multiple cerebral infarction are shown in FIGS. 7-11. Experimental results were statistically analyzed using IBM SPSS 21.0 software. The differences between groups were compared by one-way ANOVA or two-way ANOVA (water maze directional navigation) and LSD test. Experimental data were expressed as "mean±SEM", $P<0.05$, which means the results showed statistically significant differences.

The results show that compound 4 can improve the spontaneous alternating reaction rate in the Y maze, the priority index and discrimination coefficient of rats to new objects in the new object discrimination experiment, the total swimming distance of model rats in the water maze test experiment, the escape latency of directional navigation, the swimming time and percentage of swimming distance in the target quadrant, the number of times of crossing the platform, and the number of errors of rats entering the dark room in the dark avoidance experiment (see Table VII below). These results suggest that compound 4 may improve working memory, image recognition and memory, spatial memory and long-term memory impairment in the rat model of dementia caused by multiple infarction.

TABLE VII

Results of cognitive tests in a rat model of dementia caused by multiple cerebral infarction in Example 19 (n = 12-14).

| | Compared with model group | |
|---|---|---|
| Parameter | Sham operation group | Test group |
| Spontaneous alternating response rate | p < 0.001 | p < 0.001 |
| Priority index for new objects | p < 0.001 | p < 0.05 |
| Discrimination coefficient for new objects | p < 0.001 | p < 0.05 |
| Swimming time in target quadrant | p < 0.05 | p < 0.05 |
| Percentage of swimming distance | p < 0.001 | p < 0.001 |
| Times of threading | p < 0.01 | p < 0.05 |
| The incubation period for entering the darkroom | p < 0.01 | p < 0.05 |
| Priority index for new objects | p < 0.01 | p < 0.01 |
| Discrimination coefficient for new objects | p < 0.01 | p < 0.05 |

The results show that compound 4 significantly increased the ATP content of hippocampus and cerebral cortex, significantly reduced NO content and NOS activity, increased MBP expression, improved the ultrastructure of nerve cells, and significantly increased SYP expression and PSD95 expression (compared with the model group, compound 4 p<0.05), suggesting that compound 4 had effects of antioxidation and protection of neurons and mitochondria.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A method for treating cognitive impairment, for delaying or slowing the progression of said cognitive impairment, or for reducing the rate of decline of cognitive function, in a subject having or at risk of having said cognitive impairment or decline of cognitive function, the method comprising administering to said subject a therapeutically effective amount of an isotope-enriched compound, wherein the cognitive impairment or decline of cognitive function is caused by cerebrovascular disease, vascular dementia, stroke, global cerebral ischemia, or hypoxia and is not amyloid-β related, wherein the isotope-enriched compound has the general Formula (I) or a pharmaceutically acceptable salt or ester thereof:

(I)

where:

R¹ and R² are independently a hydrogen of natural abundance or a protecting group which have natural abundance or isotope enriched carbon and/or oxygen, said protecting group being selected from acyl, thiocarbonyl, and carbamoyl groups;

R is a hydrogen of natural abundance, or a deuterium (D), or a combination thereof; and X is a nitrogen of natural abundance or $^{15}N$, or a combination thereof;

provided that at least one of X, R, R¹ and R² comprises an atom that is not of natural abundance.

2. The method of claim 1, wherein the isotope-enriched compound is:

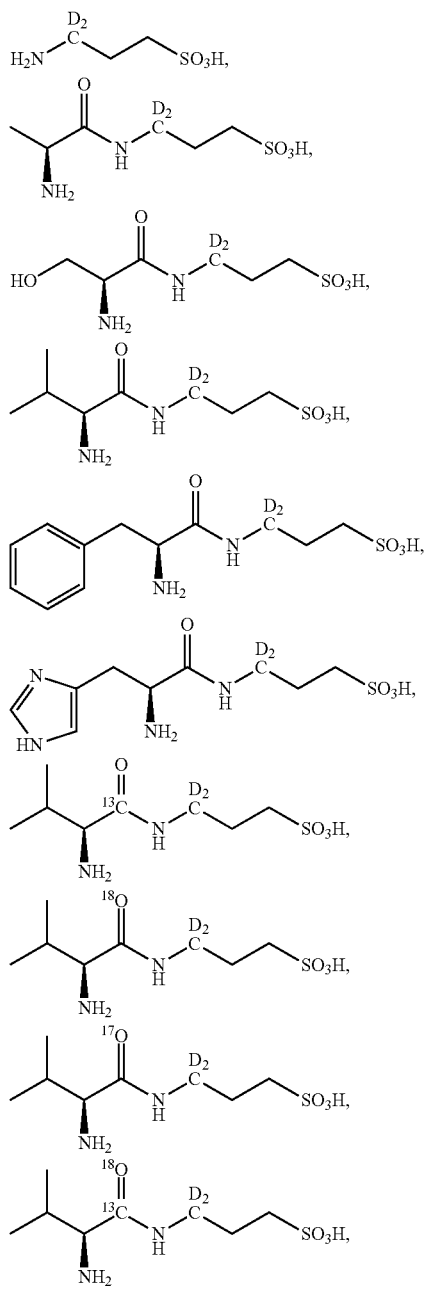

-continued

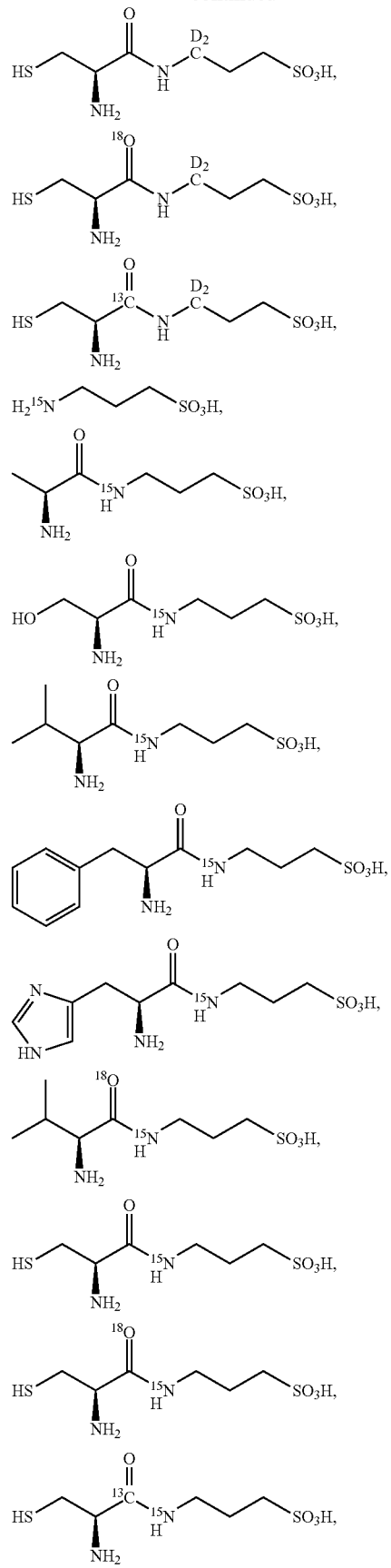

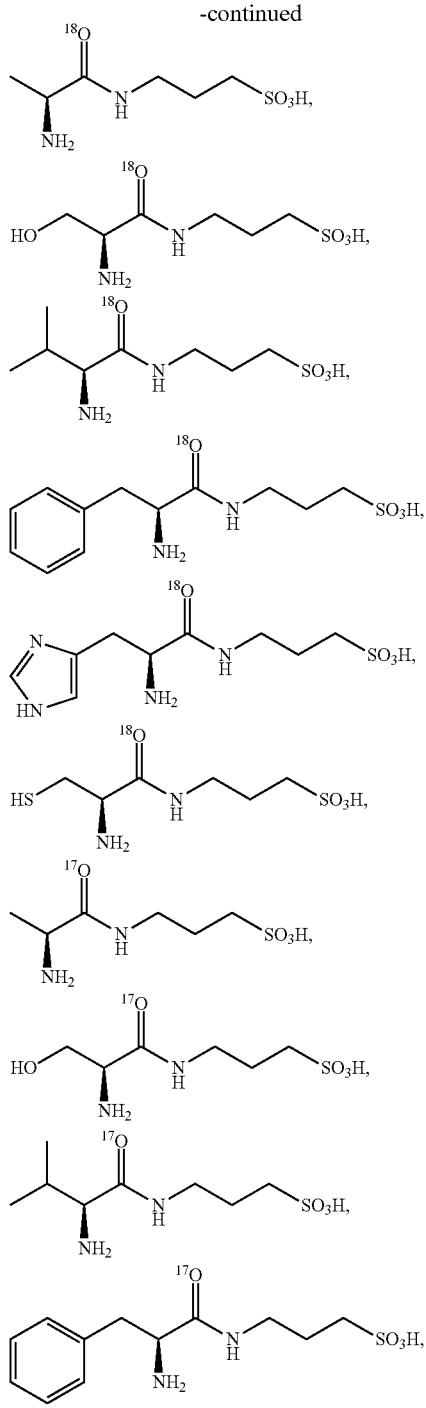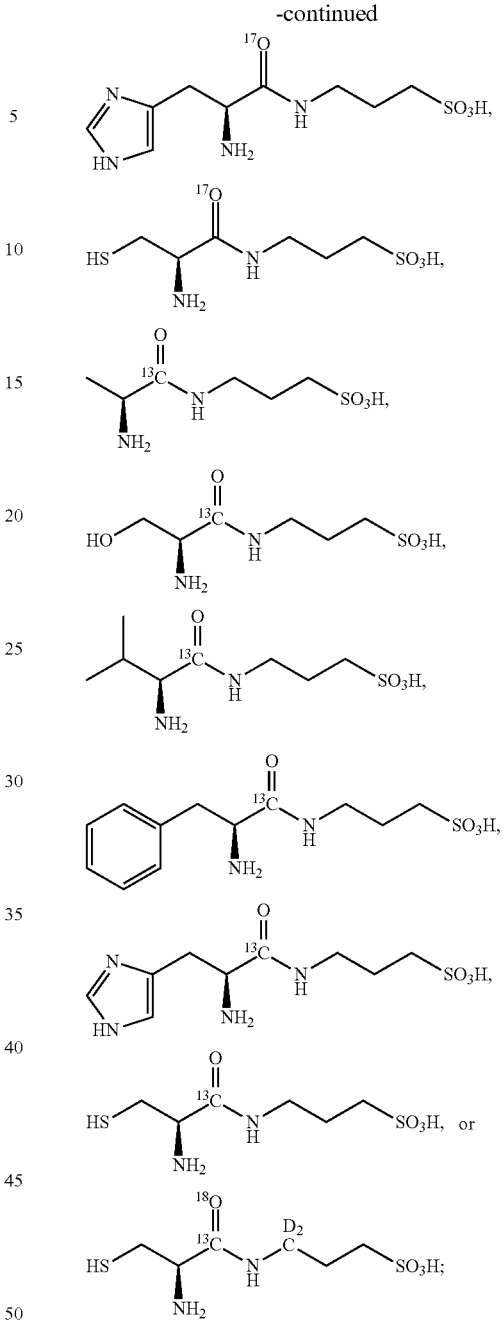
or a pharmaceutically acceptable salt or ester thereof.
* * * * *